United States Patent [19]

Schneck et al.

[11] Patent Number: 6,015,884
[45] Date of Patent: Jan. 18, 2000

[54] SOLUBLE DIVALENT AND MULTIVALENT HETERODIMERIC ANALOGS OF PROTEINS

[75] Inventors: Jonathan Schneck, Silver Spring; Sean O'Herrin, Baltimore, both of Md.

[73] Assignee: The Johns Hopkins University, Baltimore, Md.

[21] Appl. No.: 08/828,712

[22] Filed: Mar. 28, 1997

Related U.S. Application Data

[60] Provisional application No. 60/014,367, Mar. 28, 1996.

[51] Int. Cl.$^7$ .............................. C07K 16/00; C12P 21/08
[52] U.S. Cl. ...................................... 530/387.3; 530/388.1
[58] Field of Search ............................... 530/387.3, 388.1

[56] References Cited

FOREIGN PATENT DOCUMENTS

93/10220  5/1993  WIPO .
96/04314  2/1996  WIPO .

OTHER PUBLICATIONS

J. Dal Porto et al. "A soluble divalent class I major historcompatibility complex molecule inhibits alloreactive T cells at nanomolar concentrations" Proceedings of the National Academy of Science of the USA vol. 90, No. 14, Jul. 15, 1993 pp. 6671–6675.

T. Johansen et al., "Potent inhibition of alloreactive T cells by nanomolar concentrations of a divalent soluble class I MHC molecule" The Journal of Immunology, vol. 150, No. 8, part 2, Apr. 15, 1993, p. 83A.

C. Gregoire et al. "Engineered secreted T–cell receptor alpha–beta heterodimers" Proceedings of the National Academy of Sciences of the USA vol. 88, No. 18, Sep. 15, 1991, pp. 8077–8081.

D. Eilat et al. "Secretion of a soluble, chimeric gamma–delta T–cell receptor–immunoglobulin heterodimer" Proceedings of the National Academy of Sciences of the USA, vol. 89, No. 15, Aug. 1, 1992, pp. 6871–6875.

S. Weber et al. "Specific low–affinity recognition of major histocompatibility complex plus peptide by soluble T–cell receptor" Nature, vol. 356, No. 6372, Apr. 30, 1992, pp. 792–976.

H–C Chang et al. "A general method for facilitating heterodimeric pairing between two proteins: Application to expression of alpha and beta T–cell receptor extracellular segments" Proceedings of the National Academy of Sciences of the USA, vol. 91, Nov. 1994, pp. 11408–11412.

S. O'Herrin et al. "Expression and analysis of soluble MHC– and TcR–immunoglobulin super dimers" The FASEB Journal, vol. 10, No. 6, Apr. 30, 1996 p. A1473.

J. Schneck et al. "Specific inhibition of graft rejection by soluble MHC superdimers" The FASEB Journal, vol. 10, No. 6, Apr. 30, 1996, p. A1473.

M. Lebowitz et al. "Specificity of soluble 2C TcR/Ig super–dimers for peptide/MHC complexes" The FASEB Journal, vol. 10, No. 6, Apr. 30, 1996, p. A1178.

*Primary Examiner*—Paula K. Hutzell
*Assistant Examiner*—Geetha P. Bansal
*Attorney, Agent, or Firm*—Banner & Witcoff, Ltd.

[57] ABSTRACT

Specificity in immune responses is in part controlled by the selective interaction of T cell receptors with their cognate ligands, peptide/MHC molecules. The discriminating nature of this interaction makes these molecules, in soluble form, good candidates for selectively regulating immune responses. Attempts to exploit soluble analogs of these proteins has been hampered by the intrinsic low avidity of these molecules for their ligands. To increase the avidity of soluble analogs for their cognates to biologically relevant levels, divalent peptide/MHC complexes or T cell receptors (superdimers) were constructed. Using a recombinant DNA strategy, DNA encoding either the MHC class II/peptide or TCR heterodimers was ligated to DNA coding for murine Ig heavy and light chains. These constructs were subsequently expressed in a baculovirus expression system. Enzyme-linked immunosorbant assays (ELISA) specific for the Ig and polymorphic determinants of either the TCR or MHC fraction of the molecule indicated that infected insect cells secreted approximately 1 μg/ml of soluble, conformationally intact chimeric superdimers. SDS PAGE gel analysis of purified protein showed that expected molecular weight species. The results of flow cytometry demonstrated that the TCR and class II chimeras bound specifically with high avidity to cells bearing their cognate receptors. These super–dimers will be useful for studying TCR/MHC interactions, lymphocyte tracking, identifying new antigens, and have possible uses as specific regulators of immune responses.

10 Claims, 16 Drawing Sheets

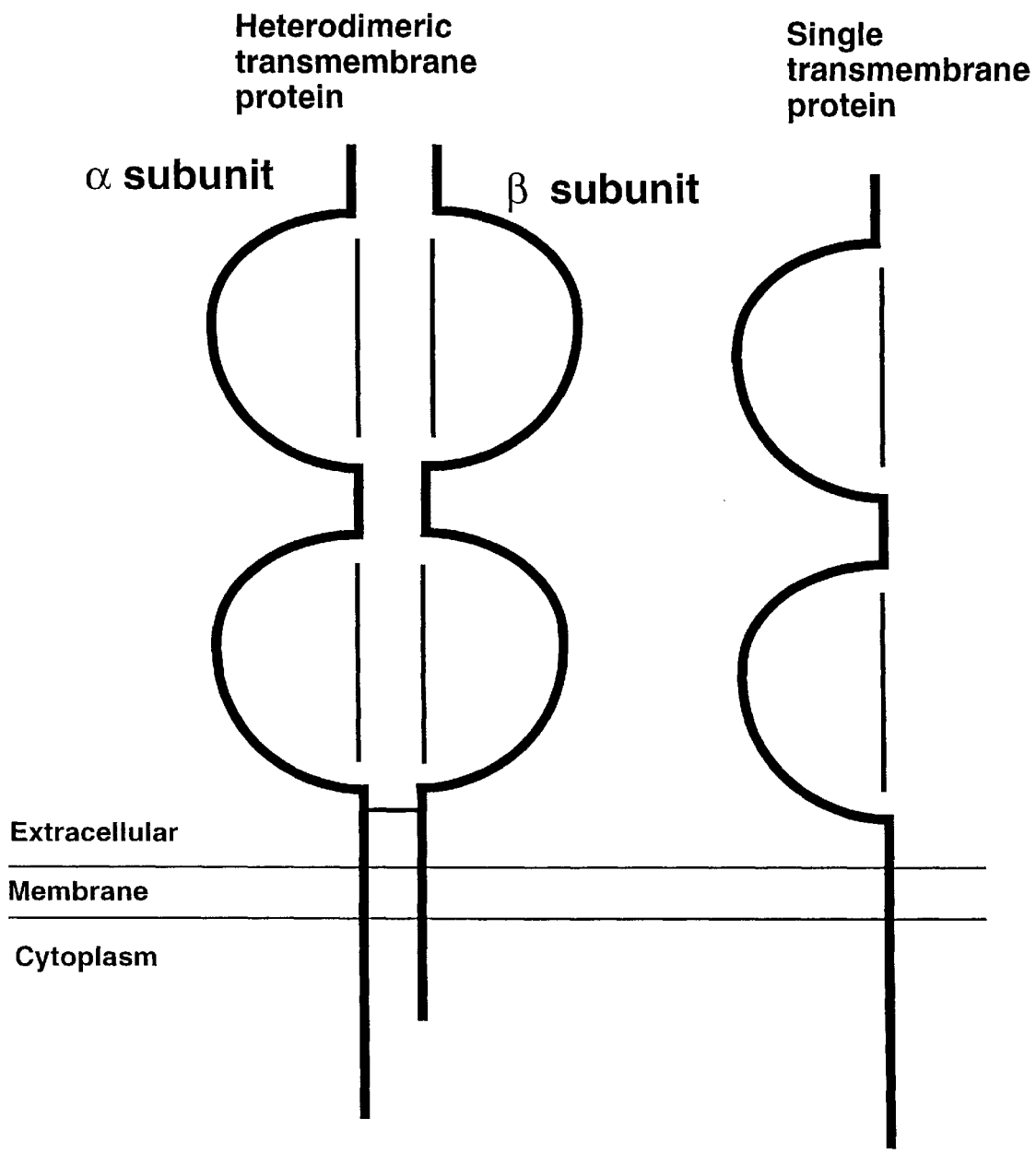
FIG. 1A A typical configuration of a heterodimeric double transmembrane protein Heterodimeric transmembrane protein made divalent and soluble by covalent linkage of outer-membrane region to antibody

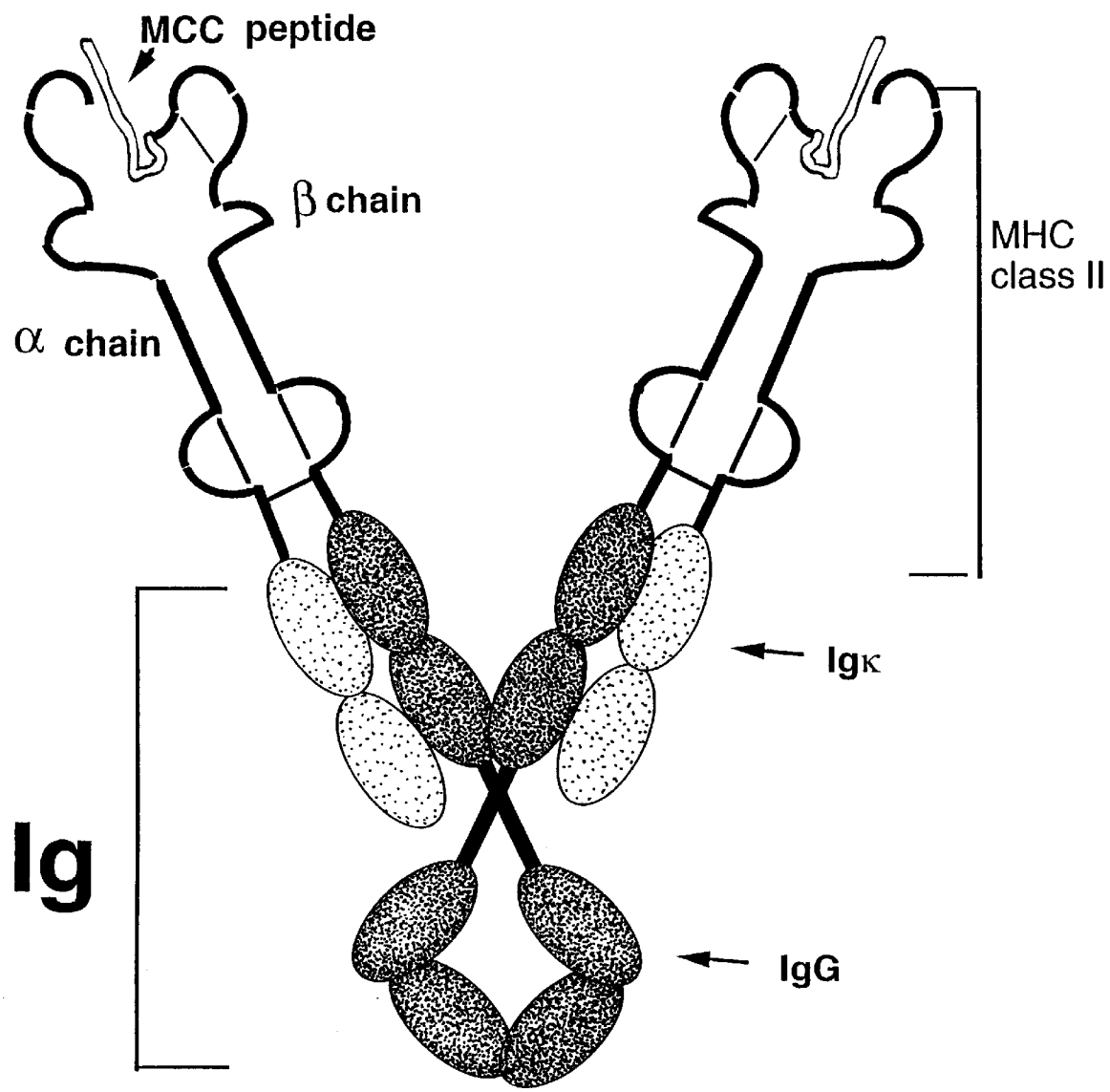
FIG. IC
Outer-membrane region of MHC class II covalently linked to an antibody Expression vector encoding soluble divalent heterodimeric proteins X and Y are cDNA derived from clones encoding any polypeptides of interest so long as they are derived from a heterodimeric protein forming a binding site. Both original polypeptide chains are from transmembrane polypetides.

FIG. 3 DNA sequences introduced into plasmids to construct soluble divalent versions of I-E$^k$ and 2C TcR.

Oligo nucleotides used to introduce the mutations outlined in Figure 2 were:

5' IgG1 mutation:

ctgtcagtaactgcaggtgtccactctggtaccagcggtgaggttcagcttcagcagtctggagc;

3' IgG1 mutation:

agcctctcccactctcctggtaaatgagcatgctctcagtgtccttggagccctctggtc;

5'Igk mutation:

ctgttgctctgttttcaaggtaccaggtgtggaagcttgggaggatctgatatccagatgacgcaaactccatcc;

3' Igk mutation:

gtcaagagcttcaacaggaatgagtgttagggtaccagacaaaggtcctgagacgccaccaccagc;

3' 2C-TcR α mutation:

cagatatgaacctaa actttcaaggaggaggtacctgtcagttatgggactccgaatc;

5' 2C-TcR β mutation:

ccaaagagaccagtatcctgactcgaggaagcatgtctaacactgccttc;

3' 2C-TcRβ mutation:

ctgcaaccatcctctatgagatcggaagcttaggatctggtacctactggggaaggccaccctatatgc;

3' I-E$_\alpha$ mutation:

ggtagcgaccggcgctcagctggaattCAAGCTTCCattctctttagtttctgggaggagggt

3' I-E$^k_\beta$ mutation:

gcacagtccacatctgcacagaacaagggaggaggtaccggggatccggttattagtacatttattaag

Schematic of interactions between T cell and antigen presenting cells

FIG. 5 Detection of soluble heterodimeric proteins

FIG. 9 A comparison of 2C TcR/Ig reactivity versus mAb 30.5.7 reactivity in peptide-stabilized H-2 L^d molecules.

FIG. 10 Inhibition of *in vitro* 2C T cell-mediated lysis by soluble 2C TcR/Ig superdimers.

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 65 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "5' oligonucleotide used to
           introduce IgG1 mutation"

(iii) HYPOTHETICAL: NO (xi) SEQUENCE DESCRIPTION: SEQ ID NO:1:

CTGTCAGTAA CTGCAGGTGT CCACTCTGGT ACCAGCGGTG AGGTTCAGCT TCAGCAGTCT    60

GGAGC                                                                65

(2) INFORMATION FOR SEQ ID NO:2:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "3' oligonucleotide used to
           introduce the IgG1 mutation"

(iii) HYPOTHETICAL: NO (xi) SEQUENCE DESCRIPTION: SEQ ID NO:2:

AGCCTCTCCC ACTCTCCTGG TAAATGAGCA TGCTCTCAGT GTCCTTGGAG CCCTCTGGTC    60

(2) INFORMATION FOR SEQ ID NO:3:

(i) SEQUENCE CHARACTERISTICS:
       (A) LENGTH: 75 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "5' oligonucleotide used to
           introduce the IgK mutation"

(iii) HYPOTHETICAL: NO (xi) SEQUENCE DESCRIPTION: SEQ ID NO:3:

CTGTTGCTCT GTTTTCAAGG TACCAGGTGT GGAAGCTTGG GAGGATCTGA TATCCAGATG    60

ACGCAAACTC CATCC                                                     75

(2) INFORMATION FOR SEQ ID NO:4:

(i) SEQUENCE CHARACTERISTICS:
       (A) LENGTH: 66 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "3' oligonucleotide used to
           introduce the IgK mutation"

(iii) HYPOTHETICAL: NO (xi) SEQUENCE DESCRIPTION: SEQ ID NO:4:

GTCAAGAGCT TCAACAGGAA TGAGTGTTAG GGTACCAGAC AAAGGTCCTG AGACGCCACC    60

ACCAGC    66

(2) INFORMATION FOR SEQ ID NO:5:

(i) SEQUENCE CHARACTERISTICS:
      (A) LENGTH: 58 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "3' oligonucleotide used to
          introduce the 2C-TcR alpha mutation"

(iii) HYPOTHETICAL: NO (xi) SEQUENCE DESCRIPTION: SEQ ID NO:5:

CAGATATGAA CCTAAACTTT CAAGGAGGAG GTACCTGTCA GTTATGGGAC TCCGAATC    58

(2) INFORMATION FOR SEQ ID NO:6:

(i) SEQUENCE CHARACTERISTICS:
      (A) LENGTH: 50 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "5' oligonucleotide used to
          introduce the 2C-TcR beta mutation"

(iii) HYPOTHETICAL: NO (xi) SEQUENCE DESCRIPTION: SEQ ID NO:6:

CCAAAGAGAC CAGTATCCTG ACTCGAGGAA GCATGTCTAA CACTGCCTTC    50

(2) INFORMATION FOR SEQ ID NO:7:

(i) SEQUENCE CHARACTERISTICS:
      (A) LENGTH: 69 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "3' oligonucleotide used to
          introduce the 2C-TcR beta mutation"

(iii) HYPOTHETICAL: NO (xi) SEQUENCE DESCRIPTION: SEQ ID NO:7:

CTGCAACCAT CCTCTATGAG ATCGGAAGCT TAGGATCTGG TACCTACTGG GGAAGGCCAC    60

CCTATATGC    69

(2) INFORMATION FOR SEQ ID NO:8:

(i) SEQUENCE CHARACTERISTICS:
      (A) LENGTH: 63 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "3' oligonucleotide used to
          introduce the I-E alpha mutation"

(iii) HYPOTHETICAL: NO (xi) SEQUENCE DESCRIPTION: SEQ ID NO:8:

GGTAGCGACC GGCGCTCAGC TGGAATTCAA GCTTCCATTC TCTTTAGTTT CTGGGAGGAG    60

GGT                                                                 63

(2) INFORMATION FOR SEQ ID NO:9:

(i) SEQUENCE CHARACTERISTICS:
          (A) LENGTH: 69 base pairs
          (B) TYPE: nucleic acid
          (C) STRANDEDNESS: single
          (D) TOPOLOGY: linear (ii) MOLECULE TYPE: other nucleic acid
          (A) DESCRIPTION: /desc = "3' oligonucleotide used to
              introduce the I-E kappa beta mutation"

(iii) HYPOTHETICAL: NO (xi) SEQUENCE DESCRIPTION: SEQ ID NO:9:

GCACAGTCCA CATCTGCACA GAACAAGGGA GGAGGTACCG GGGATCCGGT TATTAGTACA    60

TTTATTAAG                                                           69

(2) INFORMATION FOR SEQ ID NO:10:

(i) SEQUENCE CHARACTERISTICS:
          (A) LENGTH: 6 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: internal (vi) ORIGINAL SOURCE:
          (C) INDIVIDUAL ISOLATE: IgG1 peptide linker (xi) SEQUENCE DESCRIPTION: SEQ ID NO:10:

Gly Gly Gly Thr Ser Gly
1               5

(2) INFORMATION FOR SEQ ID NO:11:

(i) SEQUENCE CHARACTERISTICS:
          (A) LENGTH: 6 amino acids
          (B) TYPE: amino acid
          (C) STRANDEDNESS:
          (D) TOPOLOGY: linear (ii) MOLECULE TYPE: peptide (iii) HYPOTHETICAL: NO (v) FRAGMENT TYPE: internal (vi) ORIGINAL SOURCE:
          (C) INDIVIDUAL ISOLATE: Ig kappa peptide linker (xi) SEQUENCE DESCRIPTION: SEQ ID NO:11:

Gly Ser Leu Gly Gly Ser
1               5

(2) INFORMATION FOR SEQ ID NO:12:

(i) SEQUENCE CHARACTERISTICS:

(A) LENGTH: 8 amino acids
            (B) TYPE: amino acid
            (C) STRANDEDNESS:
            (D) TOPOLOGY: linear (ii) MOLECULE TYPE: peptide (iii) HYPOTHETICAL: NO (vi) ORIGINAL SOURCE:
            (C) INDIVIDUAL ISOLATE: peptide p2Ca (xi) SEQUENCE DESCRIPTION: SEQ ID NO:12:

Leu Ser Pro Phe Pro Phe Asp Leu
1               5

(2) INFORMATION FOR SEQ ID NO:13:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (iii) HYPOTHETICAL: NO (vi) ORIGINAL SOURCE:
            (C) INDIVIDUAL ISOLATE: peptide QL9

(xi) SEQUENCE DESCRIPTION: SEQ ID NO:13:

Gln Leu Ser Pro Phe Pro Phe Asp Leu
1               5

(2) INFORMATION FOR SEQ ID NO:14:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (iii) HYPOTHETICAL: NO (vi) ORIGINAL SOURCE:
            (C) INDIVIDUAL ISOLATE: peptide SL9

(xi) SEQUENCE DESCRIPTION: SEQ ID NO:14:

Leu Ser Pro Phe Pro Phe Asp Leu Leu
1               5

(2) INFORMATION FOR SEQ ID NO:15:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (iii) HYPOTHETICAL: NO (vi) ORIGINAL SOURCE:
            (C) INDIVIDUAL ISOLATE: peptide tum (xi) SEQUENCE DESCRIPTION: SEQ ID NO:15:

Thr Gln Asn His Arg Ala Leu Asp Leu
1               5

(2) INFORMATION FOR SEQ ID NO:16:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:
        (C) INDIVIDUAL ISOLATE: peptide pMCMV (xi) SEQUENCE DESCRIPTION: SEQ ID NO:16:

Tyr Pro His Phe Met Pro Thr Asn Leu
1               5

(2) INFORMATION FOR SEQ ID NO:17:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:
        (C) INDIVIDUAL ISOLATE: peptide gp 70

(xi) SEQUENCE DESCRIPTION: SEQ ID NO:17:

Ser Pro Ser Tyr Val Tyr His Gln Phe
1               5

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:
        (C) INDIVIDUAL ISOLATE: peptide dEV-8

(xi) SEQUENCE DESCRIPTION: SEQ ID NO:18:

Glu Gln Tyr Lys Phe Tyr Ser Val
1               5

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:
        (C) INDIVIDUAL ISOLATE: peptide SIY (xi) SEQUENCE DESCRIPTION: SEQ ID NO:19:

```
Ser Ile Tyr Arg Tyr Tyr Gly Leu
1               5

(2) INFORMATION FOR SEQ ID NO:20:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (iii) HYPOTHETICAL: NO (vi) ORIGINAL SOURCE:
         (C) INDIVIDUAL ISOLATE: peptide pVSV NP(52-59)

(xi) SEQUENCE DESCRIPTION: SEQ ID NO:20:

Arg Gly Tyr Val Tyr Gln Gly Leu
1               5
```

SOLUBLE DIVALENT AND MULTIVALENT HETERODIMERIC ANALOGS OF PROTEINS

CROSS REFERENCE TO RELATED APPLICATIONS

This application is a continuation-in-part of Provisional Application Ser. No. 60/014,367, which was filed Mar. 28, 1996.

TECHNICAL FIELD

This invention is directed to compositions comprising soluble divalent and multivalent heterodimeric analogs of proteins that are involved in immune regulation and methods of making and using the same. The high affinity that these complexes have for their cognate ligands enables them to be effective competitors to T cell receptors and MHC molecules normally involved in transplant rejection and autoimmune disease. Molecules such as divalent T cell receptors may also have an impact on the diagnosis and treatment of cancer in that they may be used to augment antitumor responses, or may be conjugated to toxins which may then be used to help eliminate tumors. Use of such compositions will allow one to accomplish selective immune modulation without compromising the general performance of the immune system.

BACKGROUND OF THE INVENTION

The process of signal transduction often involves proteins that have extracellular domains, transmembrane domains, and intracellular domains. During ligand binding there is often oligomerization of receptor molecules in order to transmit effectively the signal to the intracellular component of the cell. The immune system is an excellent example of a signal transduction pathway that works by these methods (Rosen et al. J. Med. Chem. 38: 48–55).

The immune system is a defense system found in most advanced forms of higher vertebrates. A properly functioning lymphatic and immune system distinguishes between self and nonself. A healthy body protects against foreign invaders, such as bacteria, viruses, fungi, and parasites. As the body encounters foreign material (nonself), also known as an antigens, the immune system becomes activated. An antigen is recognized by characteristic shapes or epitopes on its surface. This defense mechanism provides a means of rapid and highly specific responses that are used to protect an organism against invasion by pathogenic microorganisms. It is the myriad of pathogenic microorganisms that have principally caused the evolution of the immune system to its current form. In addition to protection against infectious agents, specific immune responses are thought to be involved in surveillance against alterations in self antigens as seen in tumor development. Immune responses are also involved in the development of autoimmune disease, AIDS, as well as rejection of transplanted tissues.

Lymphocytes

Within the immune system, lymphocytes play a central role. Lymphocyte responses to foreign organisms orchestrate the effector limbs of the immune system, and ultimately, determine the fate of an infection. Lymphocytes can be divided into two main categories, B and T cells. These two types of lymphocytes are specialized in that they have different effector functions and play different roles in the development of specific immune responses. Individual lymphocytes are specialized in that they are committed to respond to a limited set of structurally related antigens. Specificity is conferred by an unique set of cell surface receptors expressed on individual lymphocytes. These receptors interact with soluble proteins, in the case of B cells, and with antigenic peptide/major histocompatibility complex (MHC) molecules in the case of T lymphocytes. The nature of the interaction with their ligands also differs between B and T cells. The antigen receptors produced by B cells, immunoglobulins (Igs), interact with their ligands with a high affinity. In contrast, T cell receptors interact with their ligands with low affinity. Thus, the T cell response is driven by the interaction of many T cell receptors (TcR) on the surface of an individual T cell interacting with multiple antigenic peptide/MHC complexes on the surface of the antigen presenting cell. Thus, these two diverse groups of cell-surface glycoproteins, the TcRs and the MHC glycoproteins, form key components of specificity in the T lymphocyte response to antigens.

T cells are a major regulatory cell of the immune system. Their regulatory functions depend not only on expression of a unique T cell receptor, but also on expression of a variety of accessory molecules and effector functions associated with an individual T cell response. Effector functions include responses such as cytotoxic responses or other responses characterized by secretion of effector molecules, i.e., lymphokines. It is this regulatory function that often goes awry in the development of autoimmune diseases. The different effector functions also play a large role in tissue graft rejection, and can be important in tumor rejection.

T cells respond to antigens in the context of either Class I or Class II MHC molecules. Cytotoxic T cells respond mainly against foreign antigens in the context of Class I glycoproteins, such as viral-infected cells, tumor antigens and transplantation antigens. In contrast, helper T cells respond mainly against foreign antigens in the context of Class II molecules. Both types of MHC molecules are structurally distinct, but fold into very similar shapes. Each MHC molecule has a deep groove into which a short peptide, or protein fragment, can bind. Because this peptide is not part of the MHC molecule itself, it varies from one MHC molecule to the next. It is the presence of foreign peptides displayed in the MHC groove that engages clonotypic T cell receptors on individual T cells, causing them to respond to foreign antigens.

Antigen-specific recognition by T cells is based on the ability of clonotypic T cell receptor to discriminate between various antigenic-peptides resident in MHC molecules. These receptors have a dual specificity for both antigen and MHC (Zinkernagel et al. Nature 248: 701–702 (1974)). Thus, T cells are both antigen-specific and MHC-restricted. A simple molecular interpretation of MHC-restricted recognition by T cells is that TcRs recognize MHC residues as well as peptide residues in the MHC-peptide complex. Independent of the exact mechanism of recognition, the clonotypic T cell receptor is the molecule that is both necessary and sufficient to discriminate between the multitude of peptides resident in MHC.

T cells can be divided into two broad subsets; those expressing α/β TcR and a second set that expresses γ/δ TcR. Cells expressing α/β TcR have been extensively studied and are known to comprise most of the antigen-specific T cells that can recognize antigenic peptide/MHC complexes encountered in viral infections, autoimmune responses, allograft rejection and tumor-specific immune responses. Cells expressing α/β TcRs can be further divided into cells that express CD8 accessory molecules and cells that express CD4 accessory molecules. While there is no intrinsic difference between the clonotypic α/β T cell receptors expressed either on CD4 and CD8 positive cells, the accessory molecules largely correlate with the ability of T cells to respond to different classes of MHC molecules. Class I MHC molecules are recognized by CD8+, or cytotoxic, T cells and class II MHC molecules by CD4+, or helper, T cells.

γ/δ T cells make up another significant population of T cells seen in circulation as well as in specific tissues. These cells are not well understood; their antigen/MHC specificity is poorly defined and in most cases their ligands are completely unknown. These cells are present in high quantities in certain tissues, including skin and gut epithelium, and are thought to play a significant role in immune responses of those organs. They have also been implicated in autoimmune responses and may be involved in the recognition of heat shock proteins. A general approach to the identification of antigenic complexes, as outlined in the present invention, would greatly facilitate understanding of how these cells influence the development of both normal and abnormal immune responses. There is a large degree of homology between both α/β and γ/δ TcR expressed in rodents and humans. This extensive homology has, in general, permitted one to develop murine experimental models from which results and implications may be extrapolated to the relevant human counterpart.

MHC Molecules in Health and Disease

Major histocompatibility antigens consist of a family of antigens encoded by a complex of genes called the major histocompatibility complex. In mice, MHC antigens are called H-2 antigens (Histocompatibility-2 antigens). In humans MHC antigens are called HLA antigens (Human-Leukocyte-associated Antigens). The loci that code for MHC glycoproteins are polymorphic. This means that each species has several different alleles at each locus. For example, although a large number of different Class I antigens may be seen in a species as a whole, any individual inherits only a single allele from each parent at each locus, and therefore expresses at most two different forms of each Class I antigen.

In the murine system, the class II MHC molecules are encoded by I-A and I-E loci, and in humans, class II molecules are encoded by the DR, DP and DQ loci. Polymorphism of class II alleles is attributed to the alpha and beta chains and specificities are designated using the nomenclature set forth by the World Health Organization (Immunogenetics (1992) 36:135).

The Role of MHC Molecules-Transplantation

MHC molecules play an essential role in determining the fate of grafts. Various species display major immunological functional properties associated with the MHC including, but not limited to, vigorous rejection of tissue grafts, stimulation of antibody production, stimulation of the mixed lymphocyte reaction (MLR), graft-versus-host reactions (GVH), cell-mediated lympholysis (CML), immune response genes, and restriction of immune responses. Transplant rejection occurs when skin, organs (e.g., kidney, liver, lung), or other tissues (e.g., blood, bone marrow) are transplanted across an MHC incompatibility. A vigorous graft rejection occurs when the immune system is activated by mismatched transplantation antigens that are present in donor tissue but not in recipient. Graft rejection may occur in the graft itself by exposure of circulating immune cells to foreign antigens, or it may occur in draining lymph nodes due to the accumulation of trapped transplantation antigens or graft cells. Because of the extensive diversity of MHC antigens, numerous specificities are possible during physiological and pathophysiologic immune-related activities, (e.g., transplantation, viral infections, and tumor development). The recognized HLA specificities are depicted, for example, in a review by Bodmer et al. (In: Dupont B. (Ed.) Immunobiology of HLA (Volume I) New York: Springer-Verlag (1989)).

The Role of MHC Molecules-Autoimmune Response

Susceptibility to many autoimmune disease shows a significant genetic component and familial linkage. Most genetic linkages of autoimmune diseases are with certain class II MHC alleles (see Table 1 for Overview). The level of association between a particular disease and an allele at one of the MHC loci is defined by a term called "relative risk". This term reflects the frequency of the disease in individuals who have the antigen compared to the frequency of the disease among individuals who lack the antigens. For example, there is a strong association with DQβ genotype in insulin-dependent diabetes mellitus; the normal DQβ sequence has an aspartic acid at position 57, whereas in Caucasoid populations, patients with diabetes most often have valine, serine or alanine at that position.

TABLE 1

Associations of HLA genotype with susceptibility to autoimmune disease

| Disease | HLA allele | Relative risk |
| --- | --- | --- |
| Goodpasture's syndrome | DR2 | 15.9 |
| Multiple Sclerosis | DR2 | 4.8 |
| Grave's disease | DR3 | 3.7 |
| Myasthenia gravis | DR3 | 2.5 |
| Systemic lupus erythematosus | DR3 | 5.8 |
| Unsulin-dependent diabetes mellisis | DR3 and DR4 | 3.2 |
| Rheumatoid arthritis | DR4 | 4.2 |
| Pemphigus vulgaris | DR4 | 14.4 |
| Addison's disease | DR3 | 8.8 |
| Dermatitis herpetiformis | DR3 | 13.5 |
| Celiac disease | DR3 | 73.0 |
| Hashimoto's thyroiditis | DR5 | 3.2 |

Regulation of Immune Reponses

Interest in analyzing both normal and abnormal T cell-mediated immune responses led to the development of a series of novel soluble analogs of T cell receptors and MHC molecules to probe and regulate specific T cell responses. The development of these reagents was complicated by several facts. First, T cell receptors interact with peptide/MHC complexes with relatively low affinities (Matsui et al Science 254:1788–1891 (1991) Sykulev et al Immunity 1:15–22 (1994) Corr et al Science 265:946–949 (1994)). In order to specifically regulate immune responses, soluble molecules with high affinities/avidities for either T cell receptors or peptide/MHC complexes are needed. However, simply making soluble monovalent analogs of either T cell receptors or peptide/MHC complexes has not proven to be effective at regulating immune responses with the required specificity and avidity.

To regulate immune responses selectively, investigators have made soluble versions of proteins involved in immune responses. Soluble divalent analogs of proteins involved in regulating immune responses with single transmembrane domains have been generated by several laboratories.

Initially, CD4/Ig chimeras were generated (Capon et al *Nature* 337:525–531 (1989); Bryn et al *Nature* 344:667–670 (1990)), as well as CR2/Ig chimeras (Hebell et al *Science* 254:102–105 (1991)). Later it was demonstrated that immune responses could be modified using specific CTLA-4/Ig chimeras (Linsley et al *Science* 257:7920–795 (1992); U.S. Pat. No. 5,434,131; Lenschow et al *Science* 257:789–791 (1992)). In addition, class I MHC/Ig chimeras were used to modify in vitro allogeneic responses (Dal Porto, supra). However, these examples include only soluble divalent analogs of single transmembrane polypeptide molecules and not chimeric molecules of heterodimeric proteins in which the heterodimer consists of α and β polypeptides that are both transmembrane polypeptides. The present invention reports the generation of soluble divalent and multivalent heterodimeric analogs of integral membrane protein complexes, which consist of alpha and beta polymorphic integral membrane polypeptides that properly fold to form a functional unit that has potential use in immune modulation.

Previously, replacement of two transmembrane domains in the generation of multivalent analogs has not been achieved. The challenge of generating these molecules lies in achieving the proper folding and expression of two polypeptides, both of which ordinarily require transmembrane domains (FIG. 1). In addition, soluble multivalent analogs of heterodimeric proteins generally have increased affinity and, therefore, are preferred therapeutic agents. These soluble protein complexes, which consist of α and β polymorphic integral membrane polypeptides that properly fold to form a functional unit, have potential use as immune modulating agents.

SUMMARY OF THE INVENTION

It is one objective of this invention to provide soluble recombinant divalent and multivalent analogs of heterodimeric proteins, which are capable of specifically binding target molecules to regulate immune responses.

It is another object of this invention to provide soluble recombinant divalent heterodimeric proteins that possess enhanced affinity for their target molecules.

It is still another object of this invention to claim a method for producing an expression vector encoding soluble divalent analogs of heterodimeric integral membrane proteins. This comprises modifying an expression vector for an immunoglobulin molecule by inserting at least two DNA sequences, such as an a polypeptide fused to an immunoglobulin heavy chain and a β polypeptide fused to an immunoglobulin light chain (FIG. 2). This could also be done by inserting at least two DNA sequences, such as a polypeptide fused to an immunoglobulin heavy chain and an a polypeptide fused to an immunoglobulin light chain. The α and β polypeptides are ones that encode a binding or recognition site. It is also possible for the fusion proteins of the present invention to be encoded by two compatible expression vectors.

A host cell containing the vector or vectors, which is capable of expressing soluble divalent heterodimeric proteins containing an α and β polypeptide subunit is also an object of this invention.

Also included in this invention is a method for inhibiting or decreasing immune responses. Specifically, antigen-specific interactions between T cells and cells presenting antigens may be inhibited using the soluble divalent analogs of either the TcR or class II MHC molecules. An example of this could be suppression of an autoimmune response as seen in Myasthenia gravis, multiple sclerosis, arthritis, and allergic diseases. Adhesion of cells mediated through the interactions of integrins can also be inhibited using soluble divalent analogs of integrin molecules. Inhibition of cytokine-mediated cell stimulation is also included, in that soluble divalent versions of cytokine receptors could bind to soluble cytokines, thereby inhibiting the ability of the cytokines to mediate cellular proliferation.

Also included in this invention is a method for augmenting immune responses. Specifically, antigen-specific interactions between T cells and cells presenting antigens may be augmented using the soluble divalent analogs of either the TcR or class II MHC molecules immobilized on a substrate to stimulate antigen-specific T cell responses. Such a system may also be used, in the case of immobilized MHC/Ig molecules presenting antigenic peptides, to identify and purify specific T cell subsets, i.e. for the identification of the clonotypic TcR. Along the same lines, immobilized TcR/Ig may be used to identify and purify unknown peptide/MHC complexes which may be involved in cancer or infectious diseases such as AIDS. Stimulation of cells via adhesion receptors can also be accomplished using soluble divalent analogs of integrin molecules that have been immobilized on a solid substrate, such as a tissue culture plate or bead.

The invention further includes a method for treating diseases by administering soluble recombinant divalent heterodimeric analogs of proteins whereby the α and β polypeptides form a unit, and whereby the claimed constructs selectively increase or decrease cellular activation, proliferation, anergy, or deletion of specific T cell subsets. Such diseases include autoimmune disorders, transplant rejection, cancer and AIDS. Since divalent and multivalent complexes of the present invention will have increased affinity for their respective targets, administration of such compounds should selectively suppress or block T cell recognition of specific transplantation antigens and self antigens by binding to the designated target molecule and inhibiting cell-to-cell interaction.

It is also possible using techniques known in the art to conjugate toxin molecules, such as ricin and pseudomonas exotoxin, to the compounds of the present invention. The invention also includes methods of treating cancer and AIDS with such conjugate molecules. For example, following the identification of virus- or tumor-specific peptides displayed on the MHC molecules of viral-infected or tumor cells, toxin-conjugated soluble heterodimeric TCR molecules may be designed that bind to and destroy cells harboring the HIV virus, or cancerous cells, respectively. In addition, soluble divalent or multivalent MHC/IG molecules displaying tumor- or AIDS-related peptides might have potential use in immunization protocols.

Accordingly, also included in the invention are methods of identifying unknown antigens or peptides derived using soluble divalent TcR. A distinct advantage of soluble high affinity TCR/Ig chimeras is that even in the absence of any a priori knowledge about their ligands, they may be useful in defining the specific peptide/MHC ligands recognized by uncharacterized tumor-specific T cells and T cells involved in autoimmune responses. Not only are soluble divalent TCR/IG molecules efficient probes for the quantitative detection of specific peptide/MHC complexes, but due to their strong affinity for the target molecule, they will consequently play an important role in the purification of such complexes and facilitate their characterization.

Soluble divalent heterodimeric analogs of integral membrane proteins of this invention provide significant benefits because these recombinant proteins possess enhanced binding affinities for modulating immune responses. High affinity divalent ligands, such as the divalent chimeric molecules of this invention, can be used to selectively modulate specific T cell responses and to study cell-cell interactions that are driven by multivalent ligand-receptor interactions.

BRIEF DESCRIPTION OF THE DRAWINGS

FIG. 1A. A typical configuration of a heterodimeric double transmembrane protein.

FIG. 1C. Outer-membrane region of MHC class II covalently linked to an antibody.

FIG. 3. Detail of the DNA sequences introduced into the plasmid construct (SEQ ID NOs 1–9).

DETAILED DESCRIPTION OF THE INVENTION

Figure 1B:
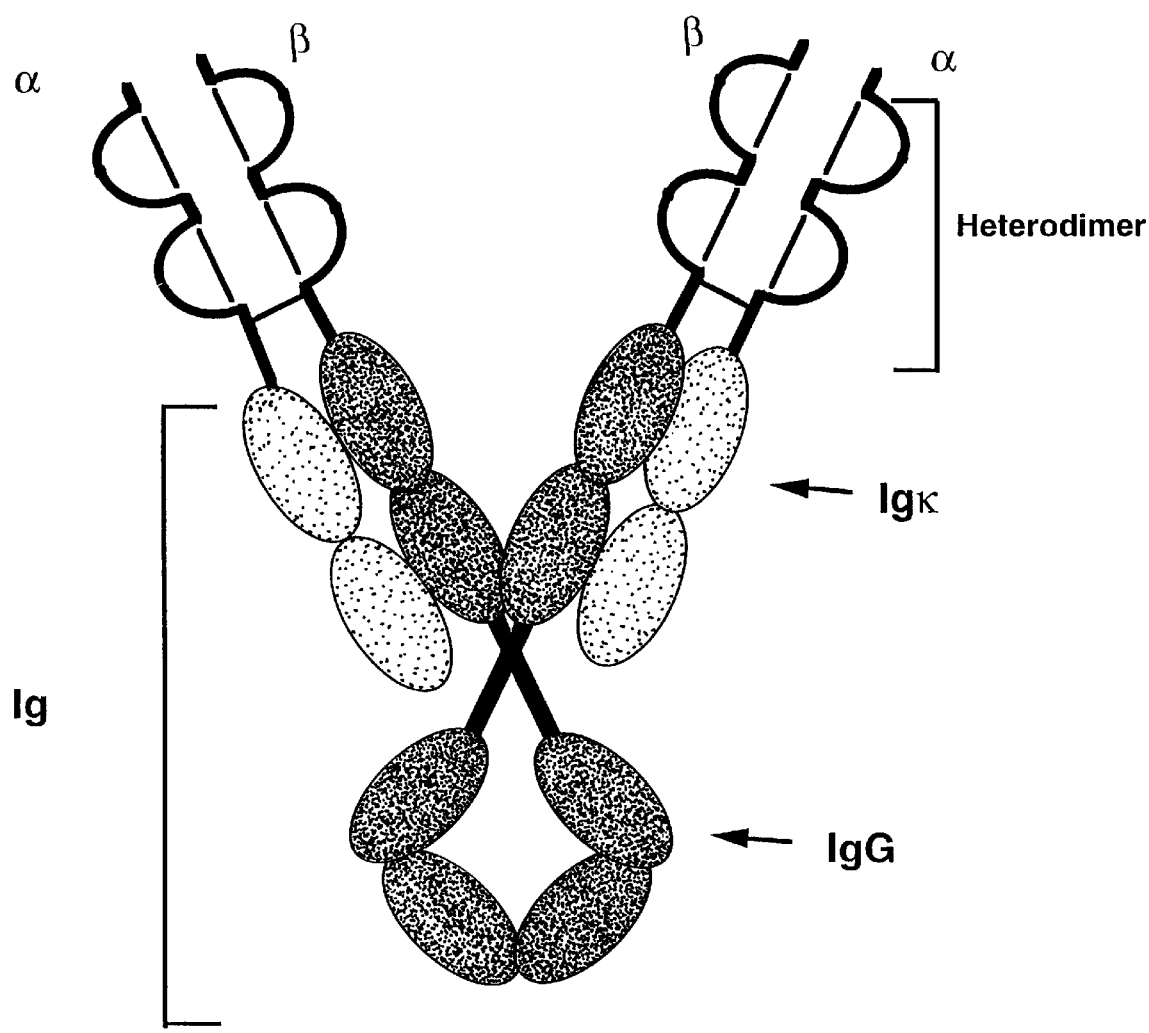
FIG. 1B. Heterodimeric transmembrane protein made divalent and soluble by covalent linkage of outer-membrane region to antibody.

Soluble recombinant divalent and multivalent analogs of heterodimeric proteins were generated that specifically bind to target molecules that regulate activities of the immune system. The construction and expression of soluble recombinant divalent and multivalent analogs of heterodimeric proteins involved linking polypeptide sequences from the heterodimeric proteins to immunoglobulin heavy and light chains. Specifically, soluble recombinant divalent and multivalent analogs of heterodimeric proteins link a polypeptide chain of a heterodimeric transmembrane protein to an immunoglobulin heavy chain and a second polypeptide chain of a heterodimeric transmembrane protein to an immunoglobulin light chain. These soluble hybrid constructs contain two or more binding sites for the same ligand.

"Polypeptide" refers to any polypeptide of a heterodimeric protein. "Polypeptide" may refer to a protein in its entirety, or to a portion thereof. Selected polypeptide sequences will minimally contain any binding site involved in a specific immune response for regulation, including regions of the protein required for proper folding and conformation of the binding site or any other region necessary for the function of the molecule. "Binding site" refers to the domain or sequence of amino acids from the protein of interest that mediates interaction or association with the ligand or target cell. The binding site may be formed from a nonconsecutive sequence of amino acids that associate in a tertiary conformation. A binding site may also be found within the extracellular domains of a glycoprotein. A glycoprotein is a protein that contains at least one carbohydrate group.

Polypeptide sequences contain about 5 amino acid sequences to about 1000 amino acid sequences. Preferably, the polypeptide sequences contain 200 amino acid sequences or less. Mammalian polypeptides are preferred, and more preferably, human polypeptides from transmembrane proteins. DNA, RNA, and amino acid sequences which have slight and non-consequential sequence variations from the actual sequences containing more two or more binding sites for the same ligand are within the scope of the present invention. Conventional abbreviations for amino acids, peptides and their derivatives are used as generally accepted in the peptide art and as recommended by the IUPAC-IUB Commission on Biochemical Nomenclature (European J. Biochem (1984) 138:9–37). "Slight and non-consequential" sequence variations mean that the homologous sequences will function in substantially the same manner to produce substantially the same proteins and polypeptides of the present invention. Functionally equivalent polypeptides are also encompassed within this invention. Conservative substitutions may be made in such amino acid sequences without losing biological or chemical functionality.

As used herein the term "soluble" means that the composition of interest is sufficiently soluble at 37° C. or in bodily fluids, plasma, etc. such that it may be used at the specified range of concentrations required to enable the composition to serve its intended function according to the present invention.

"Divalent" means that the naturally occurring or genetically engineered chimeric protein or polypeptide of interest that has two binding sites for the same ligand. This is in contrast to bifunctional in which a chimeric protein has two binding sites for different ligands on the same polypeptide. Thus all immunoglobulins are both bifunctional and also minimally divalent. There are bifunctional in that they all have at least one binding site for antigen and a separate site for Fc-receptor binding. Immunoglobulins are also minimally divalent in that they have at least two identical but separate binding sites for antigen.

"Multivalent" means that the naturally occurring or genetically engineered chimeric proteins or polypeptides of interest have more than two binding sites for the same ligand. For example, "multivalent" would encompass IgM and IgA chimeric molecules according to the present invention, which are pentavalent and tetravalent, respectively. In addition, "multivalent" might indicate a composition having more than one chimeric antibody molecule. Since each divalent heterodimeric IgG molecule has two binding sites (divalent), a chimeric antibody complex containing four IgG molecules would have eight antigen binding sites (octavalent). Similar multivalent antibody complexes that are non-chimeric have been constructed using methods known in the art. For instance, Sano and Cantor disclose a method for making a multivalent antibody U.S. Pat. No. 5,328,985 using streptavidin-proteinA, which has four or more IgG binding sites per molecule. The number of antibody molecules per conjugate molecule is controlled by mixing the streptavidin-Protein A and antibody of interest at an appropriate ratio. Other methods of conjugating antibodies known in the art could also be used to form soluble multivalent chimeric compositions according to the present invention.

"Linker" refers to the linker region inserted between the immunoglobulin molecules and the heterodimeric polypeptides. The length of the linker sequence will vary depending upon the desired flexibility to regulate the degree of antigen binding and cross-linking. The "linker" should be considered to be an optional feature. Constructs may be designed such that the heterodimeric polypeptides are directly and covalently attached to the immunoglobulin molecules without an additional linker region. If a linker region is included, this region will preferably contain at least 3 and not more than 30 amino acids. More preferably, the linker is about 5 and not more than 20 amino acids and most preferably, the linker is less than 10 amino acids. Generally, the linker consists of short glycine/serine spacers, but any known amino acid may be used.

"Immunoglobulin(s) or Ig(s)" means a group of proteins that are products of antibody secreting cells. Igs are constructed of one, or several, units, each of which consists of two heavy (H) polypeptide chains and two light (L) polypeptide chains. Each unit possesses two combining sites for antigen. The H and L chains are made up of a series of domains. The L chains, of which there are two major types ($\kappa$ and $\lambda$), consists of two domains. The H chains of Ig molecules are of several types, including $\mu$, $\delta$, and $\gamma$ (of which there are several subclasses), $\alpha$ and $\epsilon$. There are eight genetically and structurally identified Ig classes and subclasses as defined by heavy chain isotypes: lgM, IgD, IgG3, IgG 1, IgG2b, IgG2a, IgE, and IgA. Further, for example, "IgG" means an immunoglobulin of the G class, and that, "IgG1" refers to an IgG molecules of subclass 1 of the G class. "Fab" and "F(ab')$_2$" are fragments of Ig molecules that can be produced by proteolytic digestion of an intact Ig molecule. Digestion of an IgG molecule with papain will produce two Fab fragments and an Fc fragment and digestion with pepsin will produce an F(ab')$_2$ fragment and subfragments of the Fc portion.

The "transplantation antigens" referred to in the present invention are molecules responsible for graft recognition and rejection. Since the immunological status of the recipient is a critical factor affecting graft survival, diverse antigen systems may be involved in the acceptance/rejection process. These not only include the well recognized HLA system, such as class I and class II MHC molecules, but also include other minor histocompatibility antigens, such as the ABO blood group system, (including carbohydrates, which includes but is not limited to, disaccharides, trisaccharides, tetrasaccharides, pentasaccharides, oligosaccharides, polysaccharides, and more preferably, the carbohydrate $\alpha(1, 3)$ Galactosyl epitope [$\alpha(1,3)$ Gal]), autoantigens on T and B cells, and monocyte/endothelial cell antigens. Since the present invention is primarily concerned with divalent and multivalent heterodimeric compounds comprising two subunit molecules, each generally known in the native state to possess a transmembrane domain, transplantation antigens in the context of the present invention include MHC class II antigens. In clinical applications concerning treatment or therapy to inhibit or reduce graft rejection, selective suppressing antigen soecific responses are targeted. A transplantation antigen may be any class I or class II MHC molecule, or more specifically for humans, any MHC molecules including HLA specificities such as A (e.g. A1–A74), B (e.g., B1–B77), C (e.g., C1—C11), D (e.g., D1–D26), DR (e.g., DR1–DR8), DQ (e.g., DQ1–DQ9) and DP (e.g. DP1–DP6). More preferably, HLA specificities include A1, A2, A3, A11, A23, A24, A28, A30, A33, B7, B8, B35, B44, B53, B60, B62, DR1, DR2, DR3, DR4, DR7, DR8, and DR 11 (Zachary et al., Transplant. 62: 272–283). In clinical applications concerning the therapy of autoimmune disease, a transplantation antigen is any MHC class II molecule associated or linked with the disease of interest. Such transplantation antigens particularly include any D and DR allele, but DQ and DP alleles that are shown to be associated with autoimmune disease are also encompassed. Therapeutic applications involve the specific suppression of transplantation antigens using soluble proteins (also referred to as "specific antigen suppressors") of the present invention. In particular, one therapeutic application involves specific suppression of preformed anti-carbohydrate antibody responses using specific antigen suppressors.

"Heterodimeric" means that the protein of interest is comprised of two separate polypeptide chains. In this description we will consider only those polypeptide chains that have transmembrane and intracellular domains. Different classes of heterodimeric transmembrane proteins, which contain α and β polymorphic integral membrane polypeptides that bind each other forming a functional unit involved in immune recognition, include, but are not limited to, proteins such as T cell receptors, and class II MHC molecules, integrins (e.g., including more than 20 cell surface heterodimers), and cytokine receptors (e.g., IL-2, IL-3, IL-4, IL-5, IL-6, IL-7, IL-9, erythropoietin (EPO), leukemia inhibitory factor (LIF), G-CSF, Oncostatin M, ciliary neurotrophic factor (CNTF), growth hormone, and prolactin).

It is also possible for the compositions of the present invention to be prepared such that both the heavy and light immunoglobulin chains are fused to the same extracellular domain (i.e. the extracellular domain from a class I MHC molecule or glycoprotein). Protein expression and folding would then result in a chimeric <u>homotetrameric</u> composition comprising two light chains and two heavy chains, all fused to the same polypeptide.

"Integrin" refers to a class of proteins defined as having adhesive properties and known to be involved in mediating adhesion between both like and different cells. These molecules are also heterodimeric transmembrane proteins consisting of α and β polypeptides.

"Superdimer" refers to dimers of heterodimeric proteins. This term has been coined to describe what may be the conformation of MHC molecules on the surface of antigen presenting cell. In this application this term will be used to describe only soluble "superdimers", such as the soluble divalent or multivalent versions of either class II MHC or TcR molecules.

"Cytokine" refers to proteins that affect the behavior of other cells. Cytokines made by lymphocytes are often called lymphokines or interleukins, but the generic term "cytokine" is used most often in the literature. Cytokines act on specific "cytokine receptors" on the cells they affect. Cytokine receptors also belong to a family of molecules in which at least two component polypeptides are transmembrane spanning proteins. This system is central in the growth and regulation of many cell types including cells of the immune system. Cytokines/cytokine receptors include the following examples, but are not limited to this listing: I) hematopoietin family (e.g., erythropoietin(Epo)/EpoR; IL-2(T-cell growth factor)/CD25, CD122; IL-3 (multicolony CSF)/CD123; IL-4 (BCGF-1, BSF-1)/CD124; IL-5 (BCGF-2)/CD125; IL-6 (INF-$\beta_2$, BSF-2, BCDF)/ CD126, Cdw130; IL-7/ CDw127; IL-9/ IL-9R; IL-11/IL-11R, Cdw130; IL-13 (P600)/IL-13R; IL-15 (T-cell growth factor)/IL-15R; GM-CSF (granulocyte macrophage colony stimulating family)/CDw116; OSM (OM, oncostatin M)/OMR, CDw130; LIF (leukemia inhibitory factor)/LIFR, Cdw130); II) Interferon Family (e.g., IFN-γ/CD119; INF-α/CD118; INF-β/CD118); III) Immunoglobulin Superfamily (e.g., B7.1 (CD80)/CD28;CTLA-4; B7.2/CD28, CTLA-4); IV) TNF Family (e.g., TNF-α (cachectin)/p55, p75, CD120a, CD120b; TNF-β (lymphotoxin, LT, LT-α)/p55, p75, CD120a, CD120b), LT-β), CD40 ligand (CD40-L)/CD40; Fas ligand/CD95 (Fas); CD27 ligand/CD27; CD30 ligand/ CD-30; 4-1BBL/4-1BB; V) Chemokine Family (e.g., IL-8 (NAP-1)/CDw128; MP-1 (MCAP); MIP-1α; MIP-1β; RANTES); and VI) others (TFG-β; IL-1α; IL-1β; IL-10 (cytokine synthesis inhibitor F); IL-12 (natural killer cell stimulatory factor); and MIF).

Figure 1D:
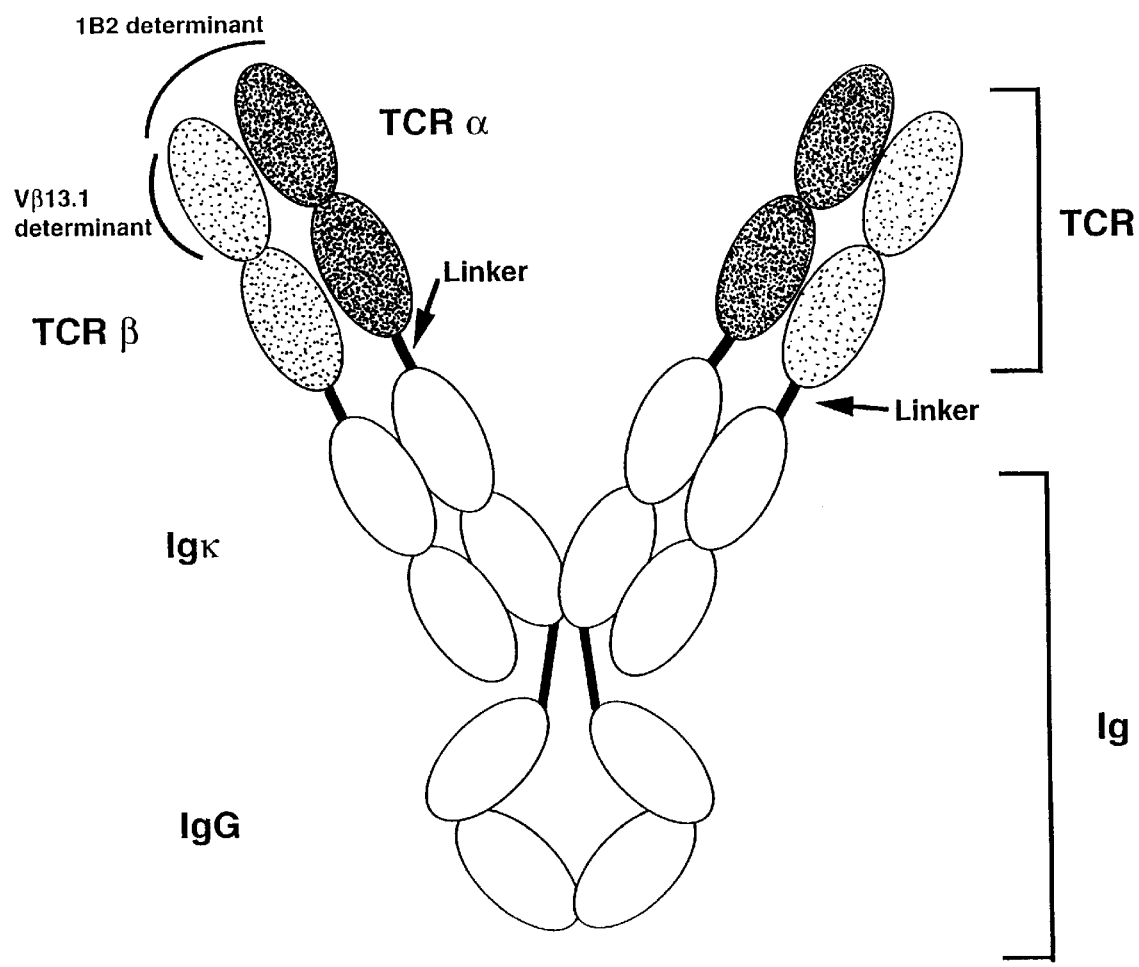
FIG. 1D. A schematic of the chimeric protein showing the TcR α polypeptide (shaded) linked to IgG1 heavy chain and TcR β polypeptide (shaded) linked to Ig kappa light chain is shown. The linkers between the chimeric chains consist of short glycine/serine spacers. Presumptive binding sites of two monoclonal antibodies (mAb), H57 (TcR specific) and 1B2 (2C TcR specific), on the putative 2C TcR/Ig structure are also noted.

DNA constructs encoding the chimeric compounds of the present invention generally comprise sequences coding for the signal sequence and extracellular domain of one polypeptide of the heterodimeric complex (i.e. TCRα or β, or MHC class II α or β) fused to the first amino acid of either the heavy or light chain immunoglobulin variable region sequence. Such a DNA construct results in the expression and secretion of a protein comprising the extracellular portion of the polypeptide of interest at the N terminus (transmembrane regions are not included) spliced to the intact variable region of the immunoglobulin molecule (see FIG. 1). Variations or truncations of this general structure in which one or more amino acids are inserted or deleted but which retain the ability to bind to the target ligand are encompassed in the present invention.

Standard Cloning Methods: The techniques for cloning and expressing DNA sequences encoding the amino acid sequences corresponding to binding sites of divalent heterodimeric analogs of integral membrane proteins, such as TcR and MHC molecules, soluble fusion proteins and hybrid fusion proteins consisting of an α and β polypeptide subunit, e.g., synthesis of oligonucleotides, PCR, transforming cells, constructing vectors, expression systems, and the like are well-established in the art, and skilled artisans are familiar with the standard resource materials for specific conditions and procedures.

In general, various expression systems are well known in the art. Prokaryotes are useful for cloning variant DNA sequences. For example, *E. coli* strain SR101 (Messing et al Nucl Acids Res 9(2):309–321 (1981), *E. coli* K12 strain 294 (ATTC No.31446), *E. coli* B, UM101, and *E. coli* χ1776 (ATTC No.31537) are particularly useful. Constructs are inserted for expression into vectors containing promoters and control sequences, which are derived from species compatible with the intended host cell. The vector ordinarily, but not necessarily, carries a replication site as well as one or more marker sequences, which are capable of providing phenotypic selection in transformed cells. For example, E. coli is typically transformed using a derivative of pBR322, which is a plasmid derived from an E. coli species (Bolivar et al Gene 2:95 (1977). pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA constructions.

Promoters suitable for use with prokaryotic hosts include, but are not limited to, the beta-lactamase and lactose promoter systems (Chang et al Nature 275:615 (1978); Goeddel et al Nature 281:544 (1979), alkaline phosphatase, the tryptophan (trp) promoter system (Goeddel et al Nucl Acid Res 8:4057 (1980), and hybrid promoters, such as the tac promoter (de Boer et al Proc Natl Acad Sci USA 80:21–25 (1983). Other functional bacterial promoters are suitable. Nucleotide sequences called linkers or adaptors are generally known which enable the skilled artisan to operably ligate DNA sequences of interest (Siebenlist et al Cell 20:269 (1980)). Promoters for use in a bacterial system will also contain a Shine-Dalgarno sequence.

In addition to prokaryotes, eukaryotic microbes, such as yeast cultures, are useful as cloning or expression hosts. In particular, Saccharomyces cerevisiae, or common baker's yeast, is commonly used (although other strains are commonly available). For expression in Sarraromyces, the plasmid YRp7, for example, is commonly used (Stinchcomb et al Nature 282:39 (1979). This plasmid already contains the trp1 gene, which provides a selection marker for a mutant strain of yeast lacking the ability to grow in tryptophan (ATTC No. 44076). The presence of the trp1 lesion as a characertistic of the yeast host cell genome then provides an effective means of selection by growth in the absence of tryptophan. Suitable promoting sequences for use with yeast hosts include the promoters for 3-phosphoglycerate kinase or other glycolytic enzymes, such as enolase, hexokinase, pyruvate kinase, and glucokinase. Other yeast promoters, which are inducible promoters having the additional advantage of transcription controlled by growth conditions, are the promoter regions for alcohol dehydrogenase 2, acid phosphatase, metallothionenin, for example. Suitable vectors and promoters for use in yeast expression are further described in R. Hitzeman et al European Patent Publication No. 73,657A.

Promoters for controlling transcription from vectors in mammalian host cells may be obtained from various sources, for example, the genomes of viruses, such as polyoma, Simian Virus 40 (SV40), adenovirus, retroviruses, hepatitis B virus, and most preferably cytomegalovirus (CMV), or from heterologous mammalian promoters, e.g. the beta actin promoter. The early and late promoters of the SV40 virus are conveniently obtained as an SV40 restriction fragment, which also contains the SV40 viral origin of replication (Fiers et al Nature 273:113 (1978). The immediate early promoter of the human CMV is conveniently obtained as a HindIII E restriction fragment (Greenaway et al Gene 18:355–360 (1982).

DNA transcription in higher eukaryotes is increased by inserting an enhancer sequence into the vector. Enhancers are cis-acting elements of DNA, usually from 10 to 300 bp, that act to increase the transcription initiation capability of a promoter. Enhancers are relatively orientation and position independent having been found 5' and 3' to the transcription unit, within an intron as well as within the coding sequence itself. Many enhancer sequences are now known from mammalian genes (globin, elastase, albumin, and insulin, for example). Typically, however, one will use an enhancer from a eukaryotic cell virus. Examples include the SV40 enhancer on the late side of the replication origin (bp 100–270), the CMV early promoter enhancer, the polyoma enhancer on the late side of the replication origin, and adenovirus enhancers.

Expression vectors used in eukaryotic host cells (yeast, fungi, insect, plant, animal, human or nucleated cells) may also contain sequences necessary for the termination of transcription, which may affect mRNA expression. These regions are transcribed as polyadenylated segments in the untranslated portion of the mRNA encoding the desired sequence. The clones containing DNA encoding soluble constructs are transfected into suitable host cells for expression. Depending upon the host cell used, transfection is performed using standard techniques (transfection into mammalian cells is accomplished using DEAE-dextran mediated transfection, $CaPO_4$ co-precipitation, lipofection, electroporation, or protoplast fusion, and still other procedures known in the art including, but not limited to, lysozyme fusion or direct uptake, osmotic or sucrose shock, direct microinjection, indirect microinjection, and/or subjecting cells to electric currents.

Peptides, proteins, or molecules of the present invention may be conjugated to a reporter group, including, but not limited to, a radiolabel (e.g., $^{32}P$), a fluorescent label, an enzyme, a substrate, a solid matrix, or a carrier (e.g., biotin or avidin) for use in the detection of specific levels of molecules or the specific binding activity of particular molecules of the present invention. Hybrid constructs of the present invention may be further modified to include toxins.

The divalent and multivalent heterodimeric compounds of the present invention may be used as immune modulating agents in methods of regulating the immune system. For example, immunoregulatory actions that may be activated or inhibited include the ability to stimulate, depress or abrogate the following immune responses: erythroid progenitor production, T-cell proliferation, hematopoiesis production, B-cell activation, class switching (e.g., IgE switch), Eosinophil growth and differentiation, T-and B-cell growth and differentiation, acute phase reaction, growth of pre-B cells and pre-T cells, mast cell activity, IL-3 and IL-4 involvement in hematopoiesis, cytokine activation or inhibition; differentiation of myeolomonocytic lineage; cancer cell growth and development; macrophage activation, MHC expression, anti-viral activity, T-cell respones, inflammation, anti-inflammation, endothelial activation, B-cell activation, apoptosis, calcium-independent cytotoxicity; chemotactic activity of neutrophils, T-cells, eosinophils, and macrphages, fever, cell (macrophage, T-cell, B-cell, neutrophils, eosinophils, natural killer cells) functions, antigen processing, cytotoxicity, and receptor crosslinking. In essence, the hybrid constructs of the present invention selectively enhances, decreases, or abrogates cellular activation, proliferation, anergy (tolerance), or deletion of specific T-cell subsets (Hewitt et al. J Exp. Med. 175:1493 (1992); Choi et al. Proc. Natl. Acad. Sci. 86:8941 (1989); Kappler et al. Science 244:811 (1989); Minasi et al. J. Exp. Med. 177:1451 (1993); Sundstedt et al. Immunology 82:117 (1994); and White et al. Cell 56:27 (1989).

In addition, the compounds of the present invention may also be used in the treatment of diseases related to immune dysfunction. Conditions which might benefit from the activation or inhibition of immune responses include, but are not limited to, the following disorders and diseases: autoimmune diseases, such as idiopathic thrombocytopenia purpura, systemic lupus erythematosus, myasthenia gravis, arthritis, autoimmune hemolysis, glomerulonephritis, multiple sclerosis, psoriasis, juvenile diabetes, primary idiopathic myxedema, systemic lupus erythematosus, autoimmune asthma, scleroderma, chronic hepatitis, Addison's disease, hypogonadism, pernicious anemia, vitiligo, alopecia areata, Coeliac disease, autoimmune enteropathy syndrome, idiopathic thrombocytic purpura, acquired spenic atrophy, idiopathic diabetes insipidus, infertility due to antispermatazoan antibodies, sudden hearing loss, sensoneural hearing loss, polymyositis, autoimmune demyelinating diseases, traverse myelitis, ataxic sclerosis, progressive systemic sclerosis, dermatomyositis, polyarteritis nodosa, hemolytic anemia, glomerular nephritis, idiopathic facial paralysis, Pemphigus vulgaris, cryoglobulinemia, and AIDS, Epstein Barr virus associated diseases, such as Sjorgren's Syndrome, rheumatoid arthritis, Burkitt's lymphoma, Hodgkin's disease, virus (AIDS or EBV) associated B cell lymphoma, chronic fatigue syndrome, parasitic diseases, such as Lesihmania and immunosuppressed disease states, such as viral infections following allograft transplantation or AIDS, cancers, chronic active hepatitis diabetes, toxic shock syndrome, food poisoning, and transplant rejection.

Since the vector constructs of the present invention incorporate a signal sequence for the secretion of each member of the chimeric heterodimeric molecule, it is possible that the therapeutic methods of the present invention may also be performed with polynucleotides or vectors designed for gene therapy. The polynucleotide may be DNA or RNA. When the polynucleotide is DNA, it can also be a DNA sequence which is itself non-replicating, but is inserted into a replicating plasmid vector. The polynucleotide may be engineered such that it is not integrated into the host cell genome. Alternatively, the polynucleotide may be engineered for integration into the chromosome provided the expression of the polypeptide may be controlled. Such regulatable gene expression systems having in vivo applicability are known in the art, and may be used in the present invention. For example, selective killing of transfected cells may be mediated by including in the polynucleotide or vector a gene sequence encoding a cytotoxic peptide such as HSV thymidine kinase (Borrelli et al. Proc. Nat. Acad. Sci. USA 85:7572, 1988). The thymidine kinase gene acts as a suicide gene for transfected cells if the patient is exposed to gancyclovir. Thus, if expression of the encoded peptides of the invention is too high, gancyclovir may be administered to reduce the percentage of cells expressing the peptides.

The compositions of the present invention, or more specifically different classes of heterodimeric transmembrane proteins or polynucleotides encoding the same, which contain $\alpha$ and $\beta$ polymorphic integral membrane polypeptides that bind each other forming a functional unit involved in immune recognition, may be made into pharmaceutical compositions with appropriate pharmaceutically acceptable carriers or diluents, such as a macromolecule, which is soluble in the circulatory system and which is physiologically acceptable where physiological acceptance means that those skilled in the art would accept injection of said carrier into a patient as part of a therapeutic regime. The carrier preferably is relatively stable in the circulatory system with an acceptable plasma half-life for clearance. Suitable carriers include, but are not limited to, water, alcoholic/aqueous solutions, emulsions, or suspensions, including saline and buffered media, and proteins such as serum albumin, heparin, immunoglobulin, polymers such as polyethylene glycol or polyoxyethylated polyols or proteins modified to reduce antigenicity by, for example, derivitizing with polyethylene glycol. Suitable carriers are well known in the art and are described, for example, in U.S. Pat. Nos. 4,745,180, 4,766,106, and 4,847,325, and references cited therein. If appropriate, pharmaceutical compositions may be formulated into preparations including, but not limited to, solid, semi-solid, liquid, or gaseous forms, such as tablets, capsules, powders, granules, ointments, solutions, suppositories, injections, inhalants, and aerosols, in the usual ways for their respective route of administration. Methods known in the art can be utilized to prevent release or absorption of the composition until it reaches the target organ or to ensure time-release of the composition. A pharmaceutically-acceptable form should be employed which does not ineffectuate the compositions of the present invention. In pharmaceutical dosage forms, the compositions may be used alone or in appropriate association, as well as in combination with, other pharmaceutically-active compounds. For example, in applying the method of the present invention for delivery of a soluble constructs of the invention, or more specifically different classes of heterodimeric transmembrane proteins, which contain $\alpha$ and $\alpha/\beta$ integral membrane polypeptides that bind each other forming a functional unit involved in immune recognition, such delivery may be employed in conjunction with other means of treatment of infectious diseases, autoimmunity, cancers, for example. The compounds of the present invention may be administered alone or in combination with other diagnostic, therapeutic or additional agents. Therapeutic agents may include cytokines or lymphokines, such as IL-2, $\alpha$-interferon and interferon-$\gamma$.

Accordingly, the pharmaceutical compositions of the present invention can be delivered via various routes and to various sites in an animal body to achieve a particular effect. Local or system delivery can be accomplished by administration comprising application or instillation of the formulation into body cavities, inhalation, or insufflation of an aerosol, or by parenteral introduction, comprising intramuscular, intravenous, peritoneal, subcutaneous intradermal, as well as topical administration.

The composition of the present invention can be provided in unit dosage form, wherein each dosage unit, e.g., a teaspoon, tablet, solution, or suppository, contains a predetermined amount of the composition, alone or in appropriate combination with other pharmaceutically-active agents. The term "unit dosage form" refers to physically discrete units suitable as unitary dosages for human and animal subjects, each unit containing a predetermined quantity of the composition of the present invention, alone or in combination with other active agents, calculated in an amount sufficient to produce the desired effect, in association with a pharmaceutically-acceptable diluent, carrier (e.g., liquid carrier such as a saline solution, a buffer solution, or other physiological aqueous solution), or vehicle, where appropriate. The specifications for the novel unit dosage forms of the present invention depend on the particular effect to be achieved and the particular pharmacodynamics associated with the pharmaceutical composition in the particular host.

Additionally, the present invention specifically provides a method of administering soluble constructs of the invention to a host, which comprises administering the composition of the present invention using any of the aforementioned routes of administration or alternative routes known to those skilled in the art and appropriate for the particular application. The "effective amount" of the composition is such as to produce the desired effect in a host which can be monitored using several end-points known to those skilled in the art. For example, one desired effect might comprise effective nucleic acid transfer to a host cell. Such transfer could be monitored in terms of a therapeutic effect, e.g., alleviation of some symptom associated with the disease being treated, or further evidence of the transferred gene or expression of the gene within the host, e.g, using PCR, Northern or Southern hybridization techniques, or transcription assays to detect the nucleic acid in host cells, or using immunoblot analysis, antibody-mediated detection, or particularized assays, as described in the examples, to detect protein or polypeptide encoded by the transferred nucleic acid, or impacted level or function due to such transfer. These methods described are by no means all-inclusive, and further methods to suit the specific application will be apparent to the ordinary skilled artisan.

The particular dosages of divalent and multivalent heterodimeric compounds employed for a particular method of treatment will vary according to the condition being treated, the binding affinity of the particular reagent for its target, the extent of disease progression, etc. However, the dosage will generally fall in the range of 1 pg/kg to 100 mg/kg of body weight per day. Where the active ingredient of the pharmaceutical composition is a nucleic acid, dosage will generally range from 1 nM to 50 $\mu$M per kg of body weight. The amounts of each active agent included in the compositions employed in the examples described herein provide general guidance of the range of each component to be utilized by the practitioner upon optimizing the method of the present invention for practice either in vitro or in vivo. Moreover, such ranges by no means preclude use of a higher or lower amount of a component, as might be warranted in a particular application. For example, the actual dose and schedule may vary depending on whether the compositions are administered in combination with other pharmaceutical compositions, or depending on individual differences in pharmacokinetics, drug disposition, and metabolism. Similarly, amounts may vary in vitro applications depending on the particular cell line utilized, e.g., the ability of the plasmid employed to replicate in that cell line. Furthermore, the amount of nucleic acid to be added per cell or treatment will likely vary with the length and stability of the nucleic acid, as well as the nature of the sequence, and is particularly a parameter which needs to be determined empirically, and may be altered due to factors not inherent to the method of the present invention, e.g., the cost associated with synthesis, for instance. One skilled in the art can easily make any necessary adjustments in accordance with the necessities of the particular situation.

The following examples merely illustrate the best mode now contemplated for practicing the invention and should not be construed to limit the invention.

EXAMPLES

Cells and Culture Conditions: RMA-S, RMA-S $L^d$, T2, T2 $K^b$, T2 Kbm3, T2 $K^{bm11}$, and RENCA cells were maintained by 1:10 passage three times weekly in RPMI-1640 supplemented with 2 mM glutamine, nonessential amino acids, 50 5 g/ml of gentamicin, 5×10-5 M 2-mercaptoethanol, and 10% fetal calf serum.

Expression of soluble 2C TcR analogs: The details of construction, expression, purification and characterization of soluble divalent 2C TcR/Ig were carried out as described elsewhere (O'Herrin et al manuscript in preparation). Briefly, to generate the soluble divalent 2C TcR, cDNAs encoding the 2C TcR $\alpha$ and $\beta$ chains were genetically linked via a six amino acid glycine/serine spacer to cDNAs encoding IgG1 heavy chains and $\kappa$ light chains, respectively (see FIG. 1 for protein schematic). Soluble monovalent 2C TcR was made and purified as previously described (Corr et al Science 265:946–949 1994).

Peptide Loading of Cells: RMA-S and T2 cell lines are defective in antigen processing and express functionally empty class I MHC on their cell surface (Spies et al Nature 355:644–646 (1992); Townsend et al Nature 340:443–448 (1989). These empty MHC molecules may be loaded with peptides as described (Catipovic et al Journal of Experimental Medicine 176:1611–1618 (1992); Townsend et al (1989) supra. Briefly, cells (RMA-S, RMA-S $L^d$, T2, T2 $L^d$, T2 Kb, T2 Kbm3 or T2 $K^{bm11}$) were cultured at 27° C. overnight. Subsequently, cells were incubated in the presence or absence of various antigenic peptides (100 5 M final concentration) for an additional 1.5 hours at 27° C. and then for one hour at 37° C.

RENCA cells were loaded with peptides by incubation with peptides (100 5 M final concentration) for >2 hrs. at 37° C. Cells were then harvested and processed for FACS analysis as described.

Measurement of the affinity of soluble 2C TcR for H-2 $L^d$ molecules: Affinities of soluble 2C TcR analogs for peptide loaded cells were determined in a competition assay with FITC-30.5.7 Fab similar to one previously described (Schlueter et al Journal of Molecular Biology 256:859–869 (1996). 30.5.7 is a monoclonal antibody that recognizes an epitope near the peptide-exposed face of H-2 $L^d$; thus 30.5.7 and 2C TcR compete for binding to the peptide exposed face of H-2 $L^d$. Kd of 30.5.7 Fab for peptide-loaded RMA-S $L^d$ cells were determined as follows. Cells (0.3×10$^6$/0 ml) were loaded with peptide as described above. Subsequently, peptide-loaded or control cells were incubated with varying concentrations of FITC-30.5.7 Fab for 1 hr. at 4° C., and then diluted 1:6 with FACS wash buffer (PBS, 1% FCS, 0.02% NaN$_3$) immediately prior to analysis by flow cytometry. Kd were estimated from a plot of 1/(mean channel fluorescence) vs. 1/[FITC-30.5.7 Fab].

Affinities of 2C TcR analogs were determined by competition with constant concentrations of FITC-30.5.7 Fab. Cells were loaded with peptide, and subsequently incubated with a constant concentration of FITC-30.5.7 Fab and varying concentration of 2C TcR analogs for 1 hour at 4° C. Cells were diluted 1:6 with FACS wash buffer immediately prior to analysis by flow cytometry. Maximal inhibition of FITC-30.5.7 Fab binding was determined by incubation in the presence of 30.5.7 mAb (75 mg). Kapp was determined from a plot of 1/(% maximal inhibition) vs. [2C TCR analog]. Kapp was corrected for the affinity of FITC-30.5.7 Fab for peptide loaded cells according to the equation Kd,TcR= Kapp/(1+([FITC 30.5.7 Fab]/Kd,30.5.7)) (Schlueter et al (1996) supra.

Direct Flow Microfluorimetry: Approximately 3×10$^5$ peptide-loaded or control cells were incubated for 60 min. at 4° C. with either ~50 mg/ml mAb 30.5.7 culture supernatants in a 30–50 ml volume, 50 ml of 2C TcR/Ig culture supernatants (10 5 g/ml final concentration), or 25–50 mg/ml purified 2C TcR/Ig in a 30 ml volume. Cells were washed once in 1×PBS, 1% FBS, 0.02% Na-azide (FACS wash Buffer) and then incubated for an additional 60 min. at 4° C. in 20 51 of a 1/20 dilution goat anti-mouse IgG-RPE (Southern Biotechnology Associates, Inc.). Cells were subsequently washed once with FACS wash buffer, resuspended in 250 ul FACS wash buffer and analyzed on a Becton Dickinson FACScan flow cytometer.

CTL Assays (Generation of CTL)—Splenocytes from 2C TCR transgenic mice (Sha et al Nature 336:73–76 (1988 ) were resuspended at 1.25×10$^6$ per ml and stimulated with 1.75×10$^6$ BALB/c splenocytes that had been exposed to 3,000 cGy radiation. On day 7, the 2C T cell-enriched cultures were restimulated at $5 \times 10^5$ per ml with $2.5 \times 10^6$ per ml BALB/c splenocytes. Experiments were performed on this and subsequent stimulationUs on day 4. All subsequent stimulation was performed with $3.75 \times 10^5$ per ml 2C splenocytes and $2.5 \times 10^6$ per ml BALB/c cells in the presence of IL-2 (5 U/ml). Assays were performed in triplicate according to established CTL protocols. Briefly, target cells ($2-4 \times 10^6$) were incubated with 100 5 $Ci^{51}[Cr]$ at 37° C. for 1 h. After three washes, cells were added to V-bottom 96 well plates ($3 \times 10^3/100$ 51) and incubated (25° C. for 1.5 h) with peptides at the indicated concentrations. 2C T cells ($3 \times 10^4/10051$) were added to targets and plates were incubated at 37° C. for 4.5 h. Maximum release was achieved by incubating targets with 5% Triton X 100. Percent specific lysis was calculated from raw data using [(experimental release—spontaneous release)/(maximum release—spontaneous release)] X 100.

General Construction and Biochemical Characterization of Chimeric Molecules

Figure 2:
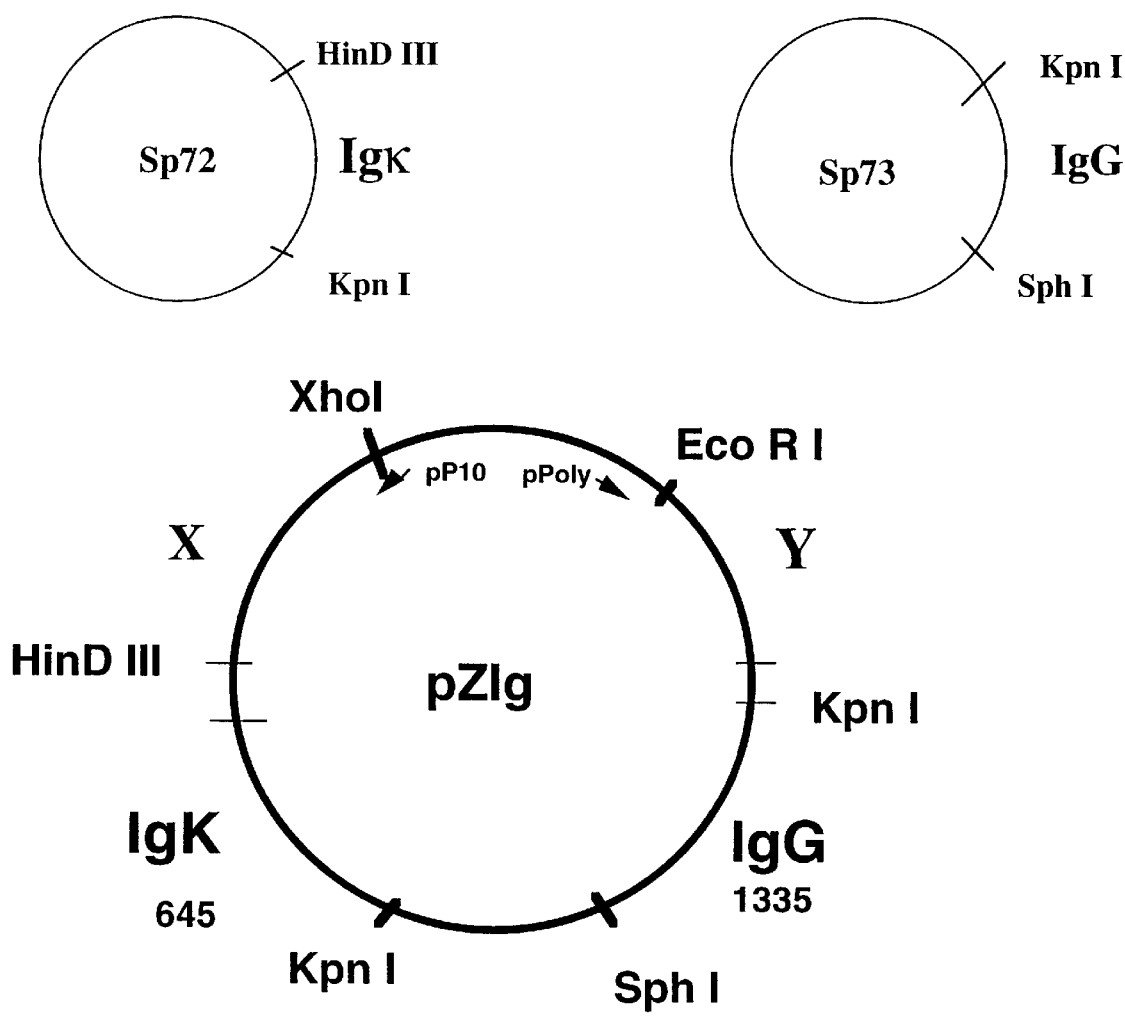
FIG. 2. Map of the expression vector, which encodes soluble divalent heterodimeric proteins. Multi-step construction schematic is shown to depict fusion of α and β polypeptide subunit linked to Ig heavy and light chains to form the chimeric Immunoglobulin molecules.
Figure 4:
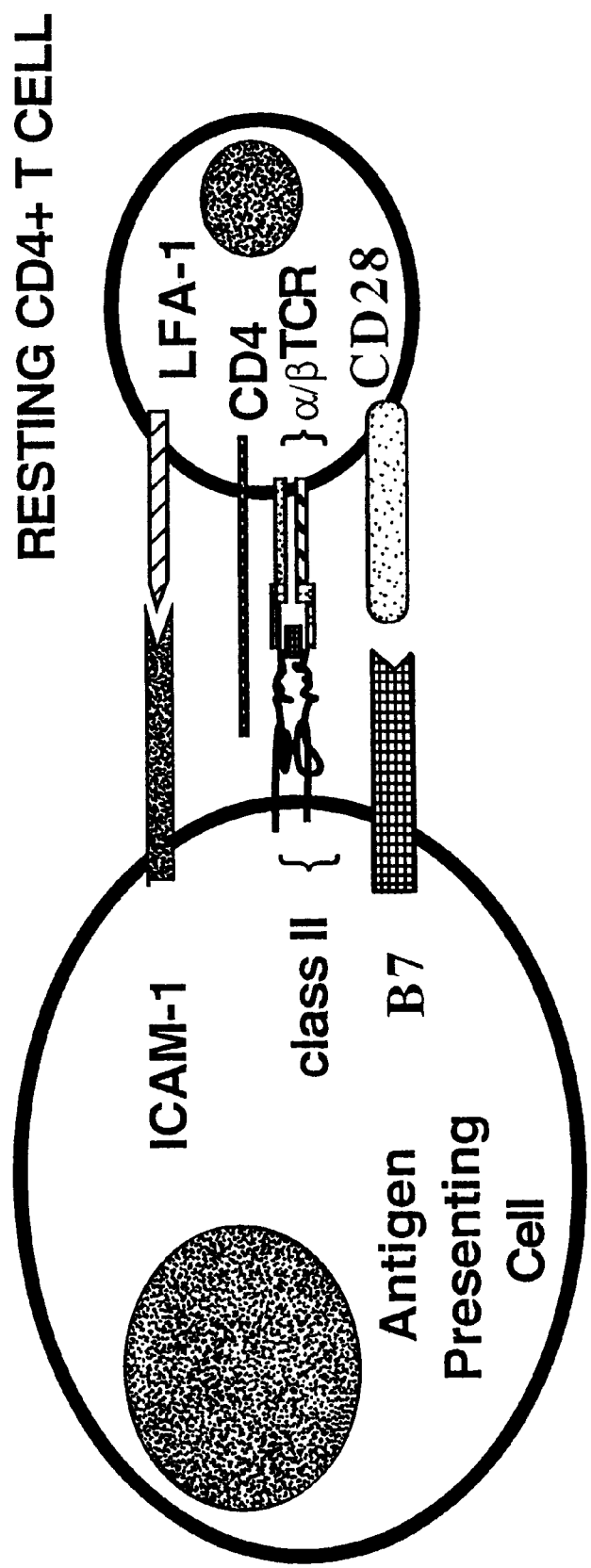
FIG. 4. Schematic of TcR/MHC interactions.

Using immunoglobulin as a backbone, a general system has been designed for expression of soluble recombinant divalent analogs of heterodimeric transmembrane proteins (FIGS. 1B–D and FIG. 2). As shown in FIG. 2, site-directed mutagenesis was used to insert restriction enzyme sites, such as KpnI and Hind III, into the 5' region of the Ig heavy and light chains, respectively. The enzyme sites were introduced immediately after the leader sequence prior to the start of the mature protein encoding the intact variable domains. This strategy leads to a generic system for expression of chimeric polypeptides and serves as a foundation molecule for construction of soluble divalent analogs of two different classes of heterodimeric proteins. The different classes of heterodimeric transmembrane proteins, which contain α and β polymorphic integral membrane polypeptides that bind each other forming a functional unit involved in immune recognition, include, but are not limited to, proteins such as T cell receptors, and class II MHC molecules, integrins, and cytokine receptors.

A multi-step construction was used to genetically fuse α and β polypeptides to Ig heavy and light chains to form the chimeric IgG molecules. As chimeric fusion partners consisted of cDNA encoding a murine IgG1 arsonate-specific heavy chain, 93G7, and K light chain, 91A3 (Haseman et al Proc Natl Acad Sci USA 87:3942–3946 (1990). Both of these Ig polypeptides have been expressed and produce intact soluble intact IgGI molecules in baculovirus infected cells. cDNA encoding the light chain clone 91A3 was modified by introduction of 5' HindIII site and linker immediately prior to position one amino acid residue, Asp, at the start of the mature protein. A KpnI restriction enzyme endonuclease site was introduced after the stop codon in the mature K polypeptide. cDNA encoding the 93G7 clone was modified but introduction of a KpnI restriction enzyme endonuclease site immediately prior to 5' to amino acid residue position Glu located at the start of the mature protein, and an SpHI restriction enzyme endonuclease site 3' to the stop codon in the mature IgGI protein.

Example 1

Construction and Expression of Soluble Divalent Class H MHC Molecules and T Cell Receptors The difficulty experienced with the construction and expression of soluble heterodimeric integral proteins, such as soluble divalent class II MHC molecules and T cell receptors (TcRs), was overcome by linking α and β chain polypeptides to immunoglobulin heavy and light chains (FIGS. 1 and 2). Using the soluble divalent TcRs, data are presented to show that soluble proteins are high affinity ligands for peptide/MHC complexes.

TcR Rationale and Construction:

The 2C TcR was selected to generate soluble divalent TcR analogs. 2C is a well characterized alloreactive, peptide-specific cytotoxic T lymphocyte (CTL) clone (Kranz et al Proc Natl Acad Sci USA 81:573–577 (1984). This clone is specific for a naturally processed endogenous peptide derived from alpha-ketoglutarate dehydrogenase bound by the murine class I molecule H-$2L^d$ (Udaka et al Cell 69:989–998 (1992). The original 2C reactive peptide, called p2Ca, identified as an eight amino acids residue. Both higher and lower affinity variants of p2Ca reactive with 2C cells have been defined (Sykulev, Immunity, supra; Sykulev et al Proc Natl Acad Sci USA 91:11487–11491 (1994) (see Table 3).

A clonotypic monoclonal antibody, 1B2, specific for the 2C TcR has also been developed (Kranz Proc. Natl Acad. Sci. USA 81:573–577 (1984). The TcR conferring 2C specificity has been cloned and transgenic mice expressing 2C TcR have also been derived (Sha et al Nature 336:73–76 (1988); Sha et al Nature 335:271–274 (1988). The above mentioned prior art makes 2C TcRs an excellent model to study.

To generate the soluble divalent TcR, cDNA encoding the TcR α and β chains of TcR was genetically linked to cDNA encoding IgGI heavy chains and K light chains, respectively. Site-directed mutagenesis was used to introduce restriction endonuclease enzyme sites into the 5' region prior to the leader sequence and into the 3' region of the TcR α and β genes immediately preceding the regions encoding the transmembrane domains (see FIGS. 1B–D for schematic of proteins, FIG. 2 for expression vector and FIG. 3 for oligonucleotides used to induce mutations). The sites introduced in the 3' region in the TcR α and β cDNA were compatible with the sites introduced into the immunoglobulin (Ig) heavy and light chain cDNA, respectively. For expression, the constructs were cloned into a modified version of baculovirus expression vector, pAcUW51, and other baculovirus expression systems (Kozono et al Nature 369:151–154 (1994). This expression vector has two separate viral promoters, polyhedron and P10, allowing expression of two polypeptides in a single virally infected cell.

The 2C TcR a chain was modified by introduction of a linker and a KpnI restriction enzyme endonuclease site immediately 3' to the Gln residue at interface between the extracellular and transmembrane domains of the a polypeptide. The 5' regions of the genes already expressed the appropriate restriction enzyme endonuclease sites and did not require any additional modifications.

The 2C TcR β chain was modified by introduction of a Xhol site 5' to the start of the signal sequence for the p chain and a HindIII restriction enzyme endonuclease site immediately 3' to the Ile residue at interface between the extracellular ad transmembrane domains of the β polypeptide.

Class II MHC Rational and Construct:

To study class II MHC molecules, the well-characterized murine I-$E^k$ molecule was chosen as a model antigen. Other class II molecules that could have been chosen include murine I-A molecules and human HLA-DR, DP, and DQ molecules. Murine I-$E^k$ is a known restriction element for a model class II antigen moth cytochrome C (MCC). Soluble monovalent versions of relevant TcR and class II MHC/peptide complexes have been generated (Wettstein et al J

*Exp Med* 174:219–228 (1991); Lin et al *Science* 249:251 (1990). T cell responses to this complex have been well characterized (Jorgensen et al *Nature* 355:224 (1992) and the affinity of specific T cell clones to MCC/I-E$^k$ complexes have been measured (Matsui *Proc. Natl. Acad. Sci.* 91:12862–12866 (1994). A genetically engineered soluble version of murine I-E$^k$ that was covalently linked to MCC has also been shown to stimulate MCC-specific T cells (Kozono, supra). Thus, this well characterized MHC system was used as a model to study the influence of divalent class II MHC on T cell reactivity.

For expression of soluble divalent class II MHC molecules, cDNA encoding the I-E$^k_\beta$ chain was genetically linked to a cDNA encoding an IgG heavy chain. A cDNA encoding an I-E$_\alpha$ chain was linked to the one encoding the kappa light chain. The 5' amino terminus of the β chain was previously genetically linked via a thrombin cleavage site to the I-E$^K$-restricted antigenic-peptide derived from MCC (81–101) (Kozono, supra). Site-directed mutagenesis was used to introduce a KpnI restriction enzyme endonuclease enzyme site into the 3' region of the I-E$^k_\beta$ immediately preceding the regions encoding the transmembrane domains. The cDNA encoding the I-E$_\alpha$ chain was modified by introduction of a HindIII restriction enzyme endonuclease immediately preceeding the transmembrane domains. The 5' I-E$_\alpha$ and I-E$_\beta$ regions of the genes did not require any additional modifications.

General Linker Region Rational and Construction:

A linker of six amino acid residues was also added at the junctions between the end of the TcR α and β and I-E α and β polypeptides and the start of the mature IgG polypeptides. For the junction with Igγ1 polypeptides the linker consists of Gly—Gly—Gly—Thr—Ser—Gly (SEQ ID NO 10). For the junction with IgK polypeptides the linker consists of Gly—Ser—Leu—Gly—Gly—Ser (SEQ ID NO 11). Oligonucleotides used to introduce all the above mutations are described in FIG. 3.

The expression vector used to generate a soluble divalent T cell receptor analog was derived from the baculovirus expression vector pAcUW51 (Pharmingen, Calif.). This vector has two separate viral promoters, polyhedron and P10, allowing one to express both chimeric polypeptide chains in the same cell. To facilitate cloning of different genes into the vector, multiple cloning sites were previously introduced after each of the promoters (Kozono, supra).

Example 2

Detection of Soluble Heterodimeric Proteins

Figure 5:
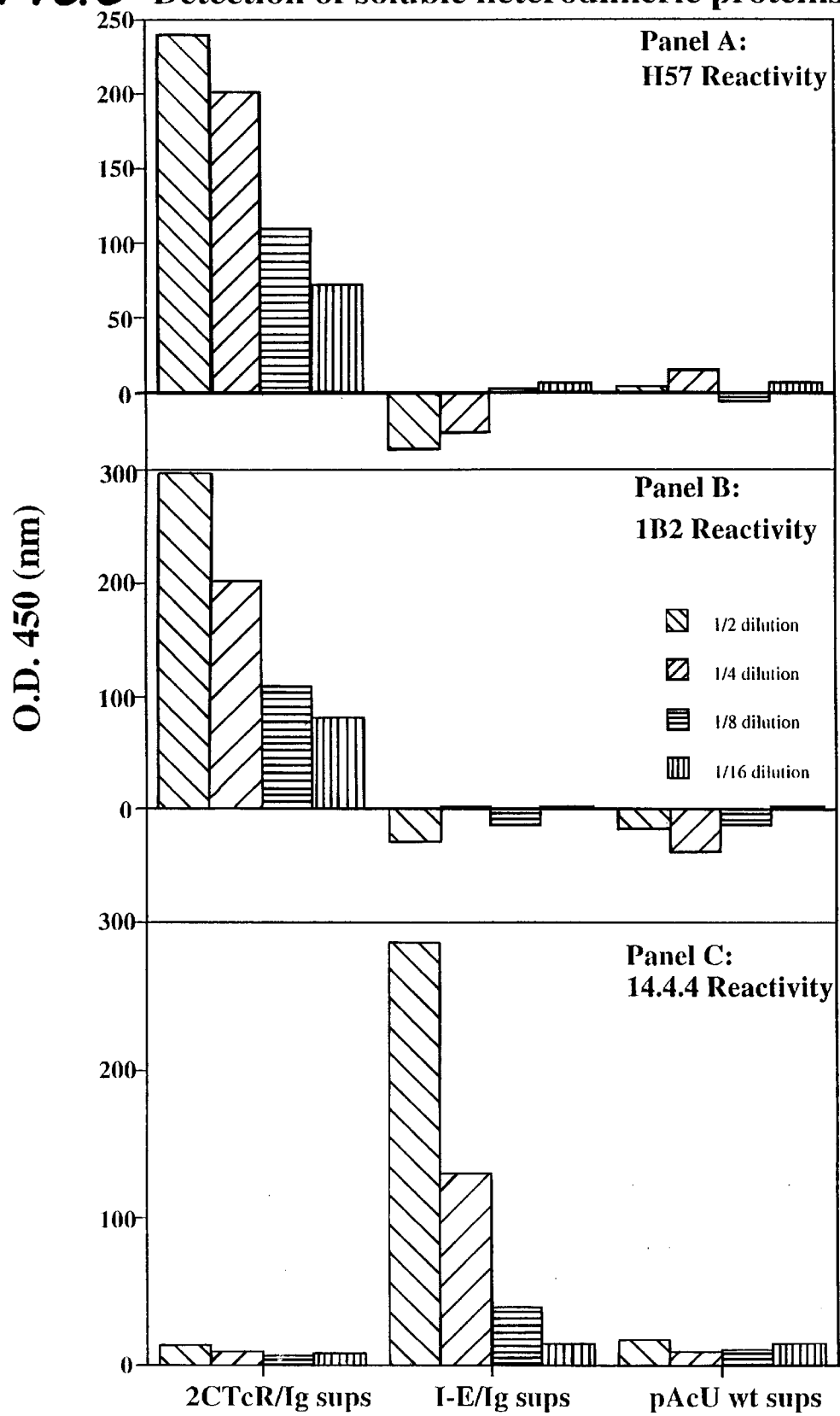
FIG. 5. Detection of soluble heterodimeric proteins by ELISA assays.

Cells infected with baculovirus containing transfer vectors encoding the soluble chimeric Ig constructs described above secrete a soluble chimeric Ig-like molecule detected by specific ELISA assays 4–5 days post infection. For 2C TcR/IgG, the assay was based on a primary antibody specific for murine IgGI Fc (plated at 10 µg/ml) and a biotinylated secondary antibody, H57 (used at 1:5000 final dilution), specific for a conformational epitope expressed on the β chain of many TcR (FIG. 5, Panel A) or biotinylated 1 B2 or a monoclonal antibody specific for a clontoypic epitope expressed on 2C TcR (FIG. 5, Panel B). For detection of I-E/IgG chimeric molecules, the same primary antibody was used and the biotinylated secondary antibody was 14.4.4, which is specific for I-Eα chain (FIG. 5, Panel C). Supernatants from infected cells were incubated for 1 hour at room temperature. Plates were washed extensively with phosphate buffer saline, incubated with the biotinylated secondary antibody for 1 hour at room temperature. The plates were then washed and incubated with HRP-conjugated strepatvidin (100 µl of a 1:10000 dilution) (Sigma, St. Louis, Mo.) for 1 hour at room temperature, washed and developed with 3, 3', 5, 5'-Tetramethylbenzidine Dihydrochloride (TMB) substrate for 3–5 minutes. Supernatants from cells infected with baculovirus containing the 2C TcR/Ig and I-E/Ig transfer vectors were compared to control supernatant from cells infected with the wild type baculovirus.

The chimeric proteins are conformationally intact as shown in FIG. 5. The soluble divalent 2C TcR/Ig is reactive with H57, a monoclonal antibody specific for a conformational epitope expressed on most TcR β chains as well as with 1B2, the anti-clonotypic monoclonal antibody determinant specific for the 2C TcR as shown in FIGS. 5A and 5B. Soluble divalent class II molecules are reactive with the conformationally dependent monoclonal antibody specific for a native alpha chain determinant only expressed on intact I-E molecules, monoclonal antibody 14.4.4 as shown in FIG. 5C. The immunoglobulin portion of the chimeric molecules is also conformationally intact. It is reactive immunoglobulin specific ELISA, as mentioned above, and can be used to purify the chimeric molecules. Protein G or arsenate-sepharose affinity purification column methods can also be used (data not shown).

Figure 6:
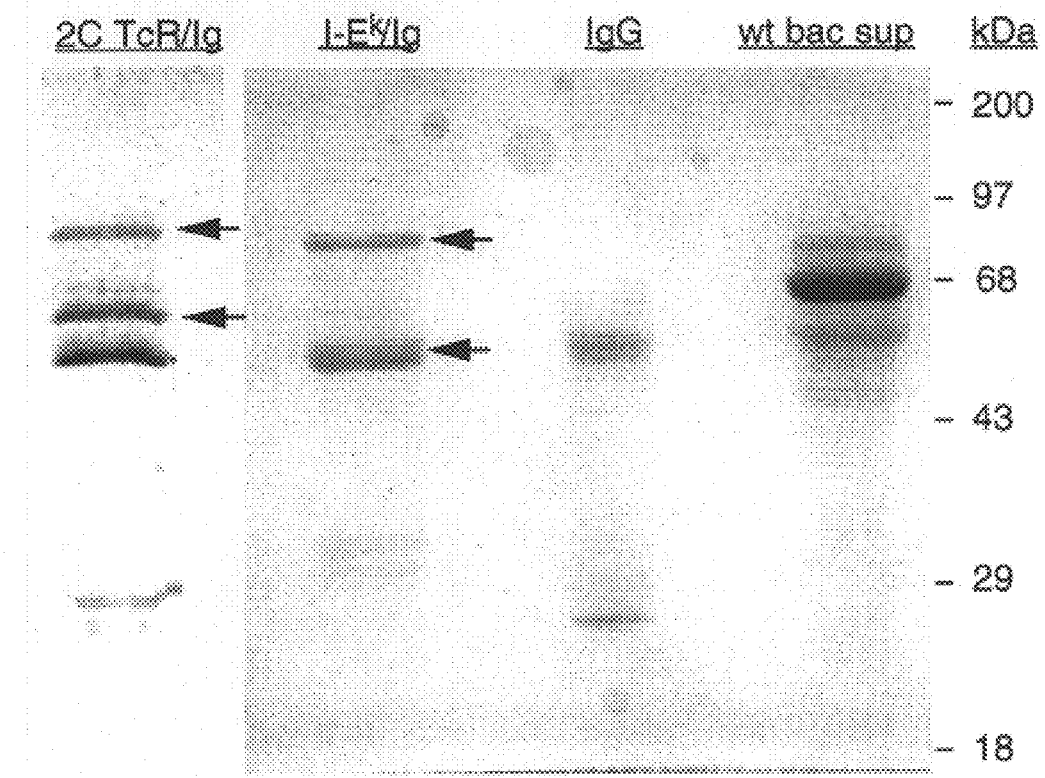
FIG. 6. SDS-PAGE analysis of I-$E^k$/Ig and 2C TcR/Ig chimeric proteins.

The purified material has the expected molecular weights when analyzed by SDS-PAGE as depicted in FIG. 6. The chimeric TcRα/IgK has an apparent molecular weight (MW) of 55,000 and the chimeric TcRα/Igγ1 has an apparent MW of approximately 89,000. The chimeric I-Eα/IgK has an approximate MW of 44,000 and the chimeric I-Eβ/Igγ1 has an apparent MW of approximately 76,000 (FIG. 6).

Example 3

Affinity measurements of soluble divalent TCR interaction with peptide/MHC complexes A competitive inhibition assay was developed to measure the affinity of soluble 2C TCR/Ig for peptide/MHC complexes. This assay, similar to one previously used to determine the affinity of soluble monovalent 2C TCR for peptide/MHC complexes (Schlueter et al *Journal of Molecular Biology* 256:859–869 (1996), is based on mAb 30.5.7 binding to a region of the a2 helix of H-2 Ld that overlaps with TCR receptor binding (Solheim et al *Journal of Immunology* 154:1188–1197 (1995); Solheim et al *Journal of Immunology* 150:800–811 (1993). Briefly, affinities of 30.5.7 Fab fragments for RMA-S L$^d$ cells were determined by direct saturation analysis of 30.5.7 Fab binding to cells analyzed by flow cytometry. Cells were incubated with increasing amounts of FITC labeled 30.5.7 Fab, and $K_d$'s were estimated from a plot of 1/MCF vs. 1/[30.5.7 Fab]. Affinities of 2C TCR analogs were determined by competition of the 2C TCR analog with a constant amount of FITC labeled 30.5.7 Fab fragments for RMA-S L$^d$ cells as described in *Methods*. $K_{app}$ was calculated from a plot of (% maximal 30.5.7 Fab binding)$^{-1}$ vs. [2C TCR analog]. The $K_{app}$ was corrected for the affinity of 30.5.7 Fab for RMA-S L$^d$ cells according to the equation $K_{d.TCR} = K_{app}/(1+\{30.5.7\ \text{Fab}\}/K_{d.30.5.7})$ (Schlueter et al., 1996). The values reported in the Table 2 are from one representative experiment that has been repeated at least three times. Each data point used in determination of the Kd is the average of duplicate points. Hence, the affinity of soluble TCR analogs was measured in terms of their inhibition of 30.5.7 binding.

To determine the affinity of the soluble 2C TCR analogs, one has to first determine the Kd of 30.5.7 Fab fragments for peptide-loaded H-2 Ld molecules. This measurement was determined by direct saturation analysis of 30.5.7-FITC Fab binding to H-2 Ld molecules on the surface of RMA-S Ld cells. RMA-S cells were chosen since these cells express empty MHC molecules that can be readily loaded with specific peptides of interest (Catipovic et al *Journal of Experimental Medicine* 176:1611–1618 (1992); Townsend et al *Nature* 340:443–428 (1989). The affinity of 30.5.7 for H-2 Ld molecules is dependent on the peptide loaded into H-2 $L^d$ (Table 2). The affinity of the 30.5.7 for QL9 loaded H-2 $L^d$ molecules is 12.2 nM while the affinities for p2Ca, pMCMV and SL9 loaded H-2 $L^d$ molecules range between 4.8–6.4 nM. These small, peptide-dependent, differences in affinity are reproducible and variations in affinity were accounted for in the competitive binding assays. These values are in good agreement with the previously measured affinities of 125I-30.5.7 Fab for the same peptide/H-2 $L^d$ complexes (8.8 to 16 nM (Schlueter et al., 1996)).

Figure 7:
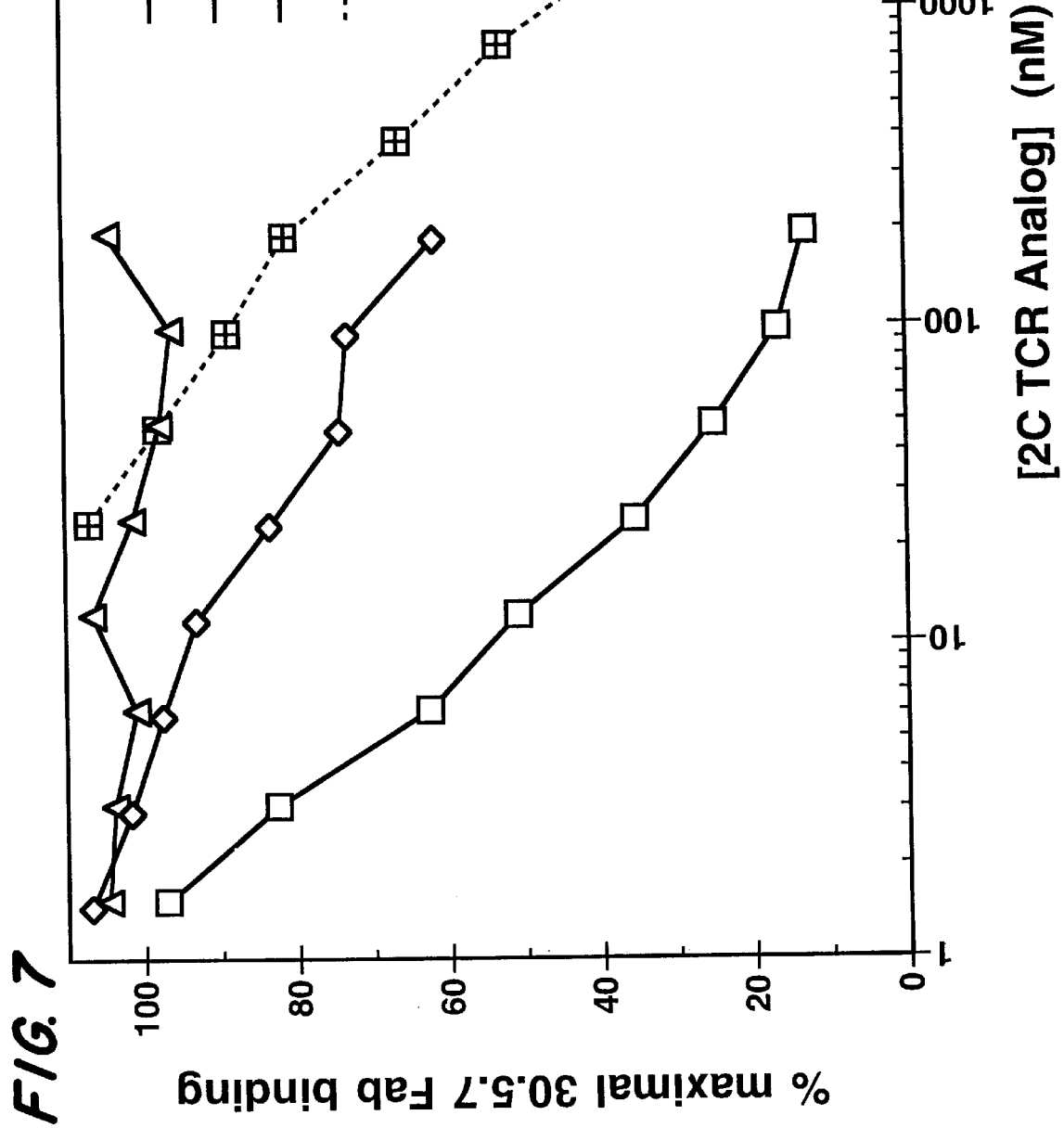
FIG. 7. Graph showing that the affinity of soluble divalent 2C TcR/Ig for peptide/H-2 $L^d$ complexes is higher than that of soluble monovalent 2C TcR is depicted in FIG. 11. RMA S-$L^d$ cells were loaded with peptides (QL9 ; p2Ca; or pMCMV) and subsequently incubated with a constant amount of FITC labeled 30.5.7 Fab and varying concentrations of either 2C TcR/Ig (solid lines) or soluble monovalent 2C TcR, sm2C TcR (dashed line) Binding of FITC-30.5.7 Fab was determined by flow cytometry. Plotted as the % maximal (no 2C TcR Analog) 30.5.7 binding vs. the concentration of 2C TcR analog. Apparent affinities were determined from a replot of 1/(% maximal 30.5.7 binding) vs [TcR Analog] see text and Table II for further discussion. Data shown are from one representative experiment that has been repeated at least three times. Each data point is the average of duplicates.

2C TCR/Ig inhibited binding of 30.5.7 Fab to H-2 $L^d$ molecules loaded with either QL9 or p2Ca peptides but did not inhibit 30.5.7 Fab binding to pMCMV loaded H-2 $L^d$ molecules (FIG. 7). The affinity of soluble divalent 2C TCR/Ig for QL9 loaded molecules is 13.3 nM (FIG. 7 and Table 2). As expected, the affinity of 2C TCR/Ig for p2Ca loaded molecules, 90 nM, is lower than that for QL9 loaded H-2 $L^d$. Although a small amount of competitive inhibition was seen with SL9 loaded cells, the affinity of the soluble divalent 2C TCR/Ig chimeras for SL9 loaded molecules is too low to be accurately measured under the conditions tested (data not shown).

In all cases analyzed, the affinity of the soluble divalent 2C TCR/Ig was significantly higher than the affinity of the soluble monovalent 2C TCR for its cognate ligand (FIG. 7 and Table 2). The affinity of soluble divalent 2C TCR/Ig was 50-fold higher for QL9-loaded H-2 $L^d$ and at least 20-fold higher for p2Ca-loaded H-2 $L^d$ molecules than that of soluble monovalent 2C TCR for the same peptide/MHC complexes (Table 2). Thus, the divalent nature of soluble 2C TCR/Ig chimeras significantly increased the affinity of the TCR analog for its cognate ligands. The finding that the chimeric molecules of the present invention demonstrate increased affinity for their specific ligands over what is seen for monovalent molecules was not an expected result. In fact, the chimeric CD4-IgG molecules disclosed in Capon et al. do not demonstrate improved target affinity, which is further evidence to the value and novelty of the compositions of the present invention.

TABLE 2

Measured Affinities of TCR analogs for peptide loaded RMA-SL$^d$ cells

| Peptide/MFIC complex | 30.5.7 Fab $K_d$ (nM) | 2C TCR/Ig $K_{app}$ (nM) | 2C TCR/Ig $K_d$ (nM) | 2C TCR/Ig $K_{app}$ (nM) | 2C-sm TCR $K_d$ (nM) |
|---|---|---|---|---|---|
| QL9 | 12.2 | 18.3 | 13.3 | 953.4 | 613.6 |
| p2Ca | 5.8 | 107.7 | 90.5 | >2000[2] | >2000[2] |
| pMCMV | 4.8 | ndc[1] | ndc[1] | —[3] | —[3] | c - no detectable competition with 30.5.7 Fab fragments
Competition was detected at the highest concentration of 2C-sm TCR used, but an accurate measure of the $K_d$ could not be determined.
not done.

Example 4

Binding Specificity of Soluble Divalent TCR Chimeras to Peptide-loaded H-2 Ld Molecules Based on the relatively high affinity of soluble divalent 2C TCR/Ig for peptide/MHC complexes, we postulated that these molecules might be useful in analysis of peptide/MHC complexes by direct flow cytometry based assays. To study peptide specificity of 2C TcR/Ig, we compared reactivity of 2C TcR/Ig with that of H-2 $L^d$ reactive mAb, 30.5.7, in direct flow cytometry assays. Specific peptides (see Table 3 for sequences) were loaded into H-2 Ld molecules on RMA-S $L^d$ cells. Peptides listed in Table 3 are a collection of H-2 $L^d$ and H-2 $K^b$ binding peptides used in analysis of the reactivity of the soluble divalent 2C TCR/Ig. Lysis and affinity data are summarized from their primary references (Corr et al., 1994; Huang et al., 1996; Solheim et al., 1993; Sykulev et al., 1994a; Sykulev et al., 1994b; Tallquist et al., 1996; Udaka et al., 1996; Van Bleek and Nathanson, 1990).

TABLE 3

Peptides used in this study*:
Their reported effectiveness in 2C CTL assays and
affinities of 2C TCR for peptide/MHC complexes.

| peptide name | peptide sequence | MHC restriction | 2C-mediated lysis | $K_d(\mu M)$ |
|---|---|---|---|---|
| p2Ca | LSPFPFDL | H-2 $L^d$ | +++ | 0.5–0.1 |
| QL9 | QLSPFPFDL | H-2 $L^d$ | ++++ | 0.066 |
| SL9 | LSPFPFDLL | H-2 $L^d$ | +/− | 71 |
| tum | TQNHRALDL | H-2 $L^d$ | na | na |
| pMCMV | YPHFMPTNL | H-2 $L^d$ | − | nd |
| gp 70 | SPSYVYHQF | H-2 $L^d$ | na | na |
| dBV-8 | EQYKFYSV | H-2 $K^b$ | − | unknown |
| dBV-8 | | H-2 $K^{bm3}$ | +++ | unknown |
| SIY | SIYRYYGL | H-2 $K^b$ | +++ | unknown |
| SIY | | H-2 $K^{bm3}$ | unknown | unknown |
| VSV NP(52–59) | RGYVYQGL | H-2 $K^b$ | − | nd |

*SEQ ID NOS 12–20, respectively
not available.
none detected. The affinity were below the sensitivity of the assay used.

Figure 8:
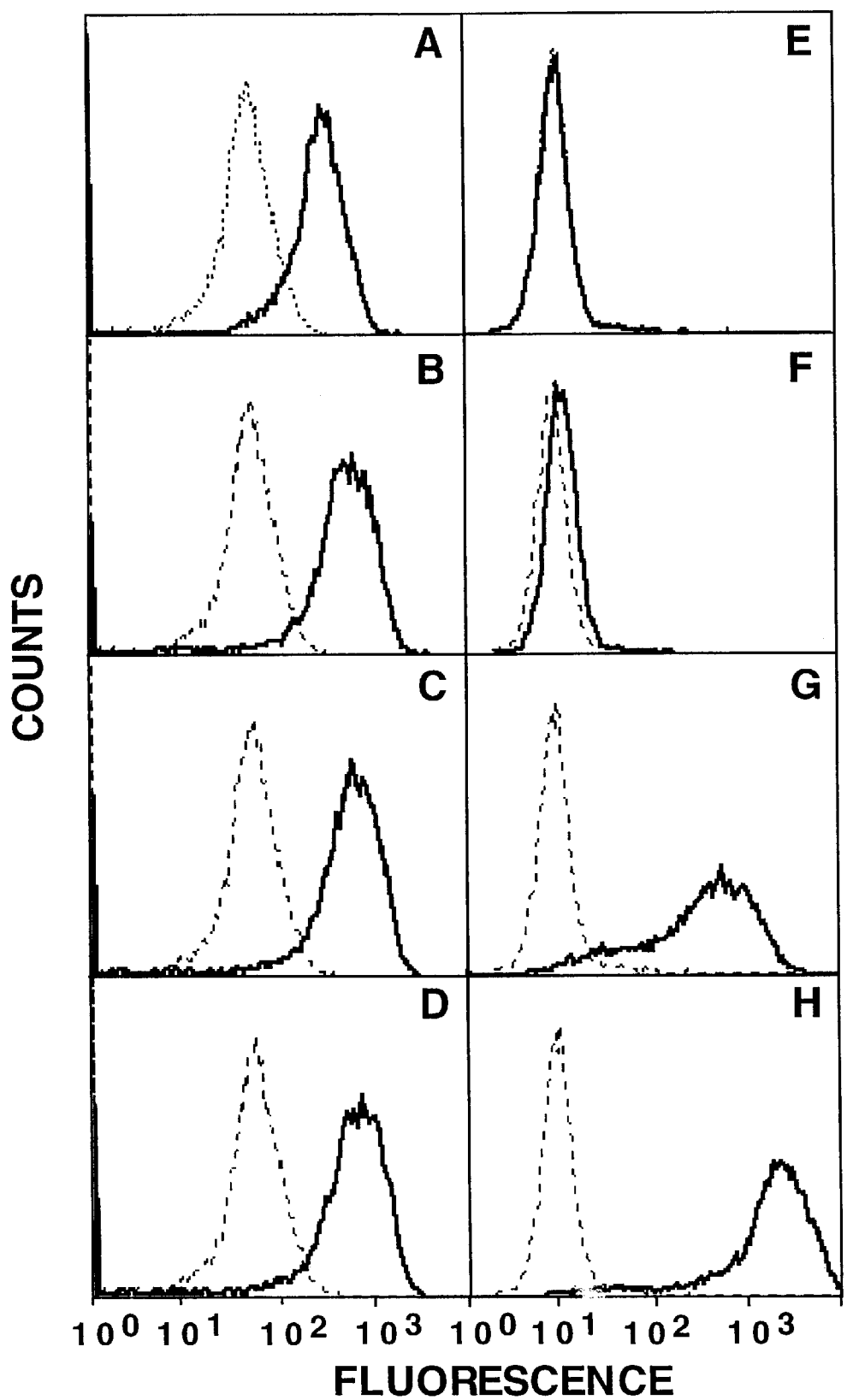
FIG. 8. Cells were then harvested as described above and processed for flow cytometry analysis. Cells were stained with either purified mAb, 30.5.7 (Panels A–D), or 2C TcR/Ig culture supernatants (Panels E–H) diluted to 20–40 μg/ml final concentration. In each panel the histogram of treated cells (solid line) is contrasted with that of cells not treated with any peptide and cultured for one hour at 37° C. (broken line). Histograms shown are from one representative experiment that has been repeated at least three times.

The temperature-dependent reactivity of RMA-S $L^d$ with 2C TCR/Ig was significantly different than the reactivity of RMA-S $L^d$ with mAb 30.5.7. As expected (Solheim et al (1995) supra; Solheim et al (1993) supra), RMA-S $L^d$ cells expressed more serologically reactive H-2 $L^d$ molecules recognized by mAb 30.5.7 on cells cultured at 27° C. than when cells were cultured at 37° C. (FIG. 8A); mean channel fluorescence (MCF) increased approximately 5 fold. Thus the epitope on H-2 $L^d$ molecules recognized by mAb 30.5.7 can be stabilized by incubating cells at low temperatures. In contrast, RMA-S $L^d$ cells expressed very low amounts of H-2 $L^d$ molecules recognized by 2C TcR/Ig on cells cultured at either 27° C. or at 37° C. (FIG. 8, Panel E). This finding is consistent with the expected peptide-dependent reactivity of 2C TcR/Ig which should not recognize unloaded MHC even when conformationally stabilized by decreased temperature.

Figure 9:
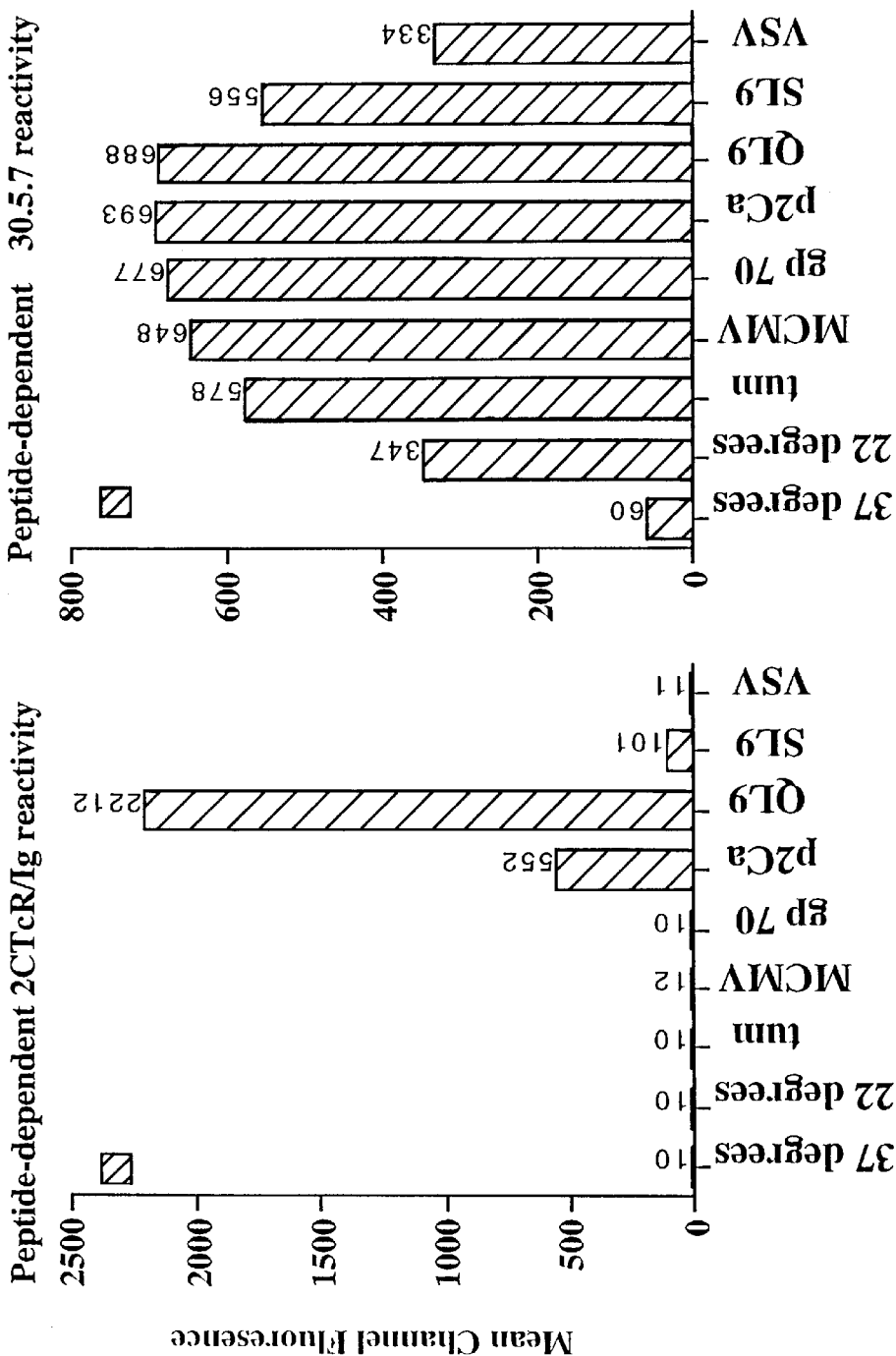
FIG. 9. A comparison of 2C TcR/Ig reactivity versus mAb 30.5.7 reactivity in peptide-stabilized H-2$L^d$ molecules. RMA-S $L^d$ cells were incubated under various conditions. Following overnight incubation of RMA-S $L^d$ cells at 27° C., cells were cultured in the presence or absence of various H-2 $L^d$ binding peptides: no peptide cells maintained at 27° C., (Panel A and E); tum⁻, (Panel B and F); p2Ca, (Panel C and G); and QL9, (Panel D and H), were added to cultures as described in section.

2C TcR/Ig reactivity also showed exquisite peptide specificity. As expected, all H-2 $L^d$-binding peptides stabilized expression of the epitope recognized by mAb 30.5.7 (FIG. 8, Panels B–D and FIG. 9). Only H-2 $L^d$ molecules loaded with 2C reactive peptides, peptides p2Ca, QL9, and SL9 expressed peptide/H-2L$^d$ epitopes that reacted with 2C TcR/Ig (FIG. 8, Panels F–H and FIG. 9). MCF increased approximately 10–200 fold, from a MCF of 10 for either unloaded cells or cells loaded with an irrelevant H-2 $L^d$ binding peptide, to as high as 2200 for RMA-S $L^d$ cells loaded with peptide QL9 (FIG. 9). The pattern of reactivity mimicked the known affinities of monovalent 2C TcR for peptide/H-2 $L^d$ complexes (see Table 3 for affinities). RMA-S $L^d$ cells loaded with peptide QL9, p2Ca, or SL9 had MCF values of 2200, 550, and 100, respectively, when stained with 2C TcR/Ig. Thus, soluble divalent 2C TcR/Ig chimeras reacted strongly with QL9/H-2 $L^d$ complexes, modestly with p2Ca/H-2 $L^d$ complexes, and weakly with SL9/H-2 $L^d$ complexes. The fact that 2C TcR/Ig bound to SL9-loaded H-2 $L^d$ molecules indicates, that even in a direct flow cytometry assay, soluble divalent 2C TcR/Ig chimeras could be used to detect specific peptide/MHC complexes that have affinities as weak as 71 mM for monovalent 2C TcR.

Example 5

Inhibition of In Vitro 2C T Cell Mediated Lysis by Soluble Divalent 2C TcR/Ig Molecules Soluble divalent 2C TcR/Ig blocks 2C reactive T cell responses. Since soluble divalent 2C TcR/Ig interacts with high avidity with H-2 $L^d$ molecules loaded with the appropriate peptides in the flow cytometry assay, it was explored whether the reagent could effectively inhibit 2C T cells in vitro cytotoxicity CTL assays. This was analyzed using a cell line derived from 2C transgenic mice to lyse tumor target cells expressing H-2 $L^d$. CTL were tested in a routine 4 hour $^{51}$Cr cytotoxicity assay. As targets for all the CTL assays, untransfected, MC57G, and $L^d$ transfected, MC57G $L^d$, cells were used as targets. The percent specific lysis was determined as: $^{51}$Cr cpm (experimental)—CPM (spontaneous)/cpm (maximum)—cpm (spontaneous). Standard errors were routinely less than 5% and spontaneous release was usually 10–15% of maximal release.

Figure 10:
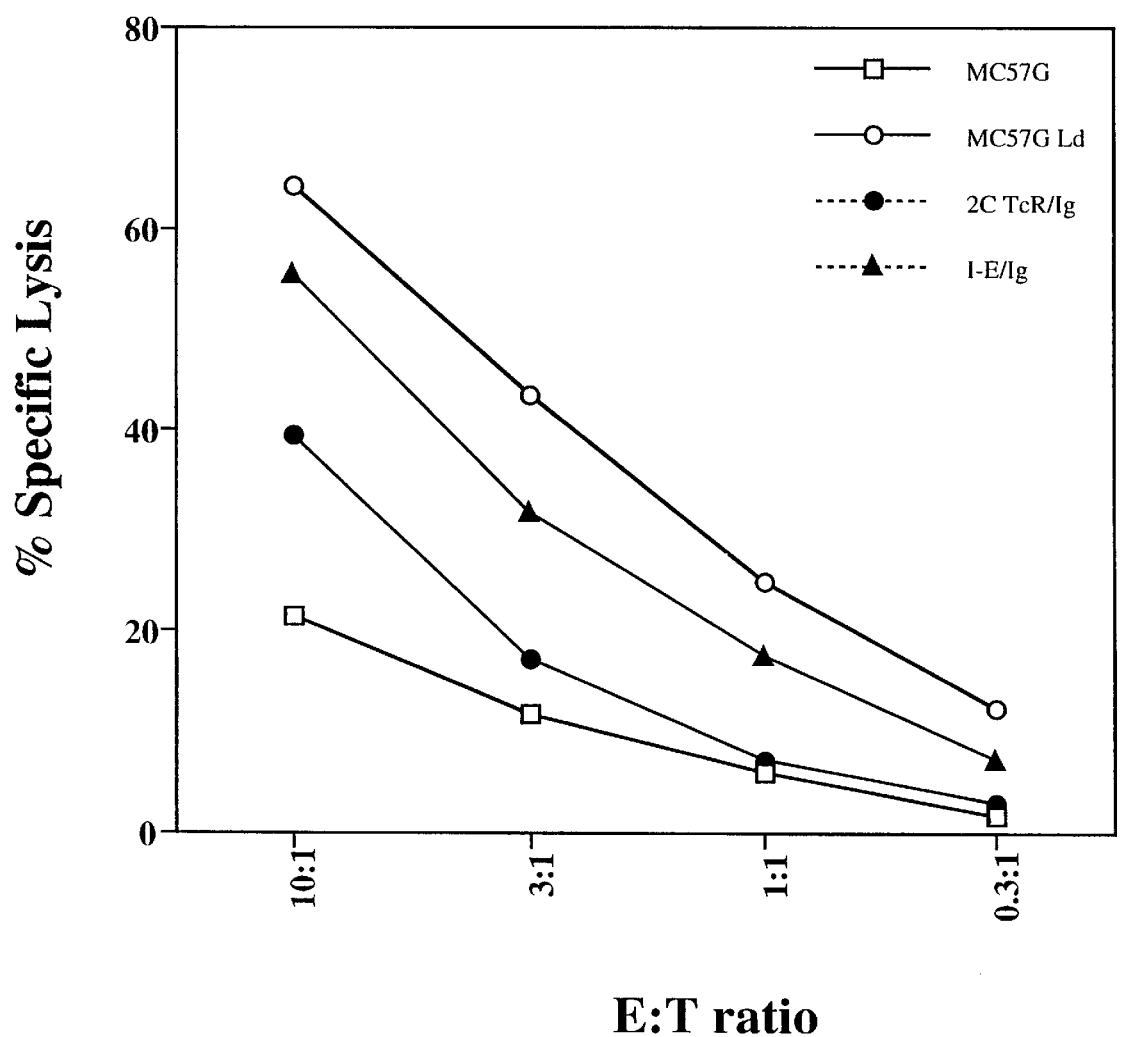
FIG. 10. Graph demonstrating inhibition of in vitro 2C T cell mediated lysis by soluble 2C TcR/Ig superdimers.

Using both untransfected MC57G and Ld transfected, MC57G $L^d$, we were able to establish a window of H-2$L^d$ specific lysis mediated by the 2C CTL line. To test the influence of 2C TcR/Ig, target cells were pretreated with either 2C TcR/Ig, or I-$E^k$/Ig and analyzed for lysis by the CTL cell line derived from 2C transgenic mice. Significant inhibition of lysis was seen at each effector to target cell ratio analyzed when cells were treated with 2C TcR/Ig (see FIG. 10). While some non-specific inhibition was seen in the I-$E^k$/Ig treated target cells, significantly more inhibition was seen in the 2C TcR/Ig treated target cells.

In this assay, the target cells were normal tumor cells that load their cell surface MHC molecules with a variety of different endogenous peptides. Using these target cells, one does not need to specifically load H-2 $L^d$ molecules with the p2Ca peptide since p2Ca or p2Ca-like peptides along with a large number of irrelevant peptides are endogenously loaded onto cellular MHC molecules. Inhibition of CTL-mediated lysis indicates that soluble divalent 2C TcR/Ig can effectively interact with the relevant peptides even within a milieu of a large number of irrelevant peptides. Thus, this approach could be used to search the universe of peptide/MHC complexes to identify only those complexes relevant to specific T cell responses of interest. In particular, these high avidity soluble analogs of heterodimeric proteins may specifically be useful in identification of unknown tumor and autoimmune antigens.

Example 6

Binding of Soluble Divalent TCR Chimeras to Self Restricted Peptide/MHC Complexes.

In addition to recognizing peptide/H-2 $L^d$ ligands, two peptides, SIY and dEV-8, that sensitize either H-2 $K^b$ or H-2 $K^{bm3}$ targets for lysis by 2C CTL have also been defined (see Table 3 for sequences). To analyze the ability of 2C TcR/Ig to bind to these alternate 2C-reactive complexes, the binding of 2C TcR/Ig to peptide loaded transfected T2 cells was studied. Since T2 cells are derived from a human cell line, T2 cells do not naturally express H-2 $K^b$ as do RMA-S cells. Thus to study the binding of 2C TcR/Ig to peptide-loaded H-2 $K^b$ or various H-2 $K^{bm}$ mutant molecules, the T2 system was chosen since it is not complicated by the expression of MHC molecules from the parental cell line. Similar to RMA-S $L^d$ cells, T2 cells also express empty MHC molecules that can be readily loaded with different peptides. For these studies peptide-loaded T2 cells transfected with: H-2 $K^b$, T2 $K^b$; H-2 $K^{bm3}$, T2 $K^{bm3}$; and H-2 $K^{bm11}$, T2 $K^{bm11}$ (Tallquist et al Journal of Immunology 155:2419–2426 (1995); Tallquist et al Journal of Experimental Medicine 184:1017–1026 (1996) were utilized.

Figure 11:
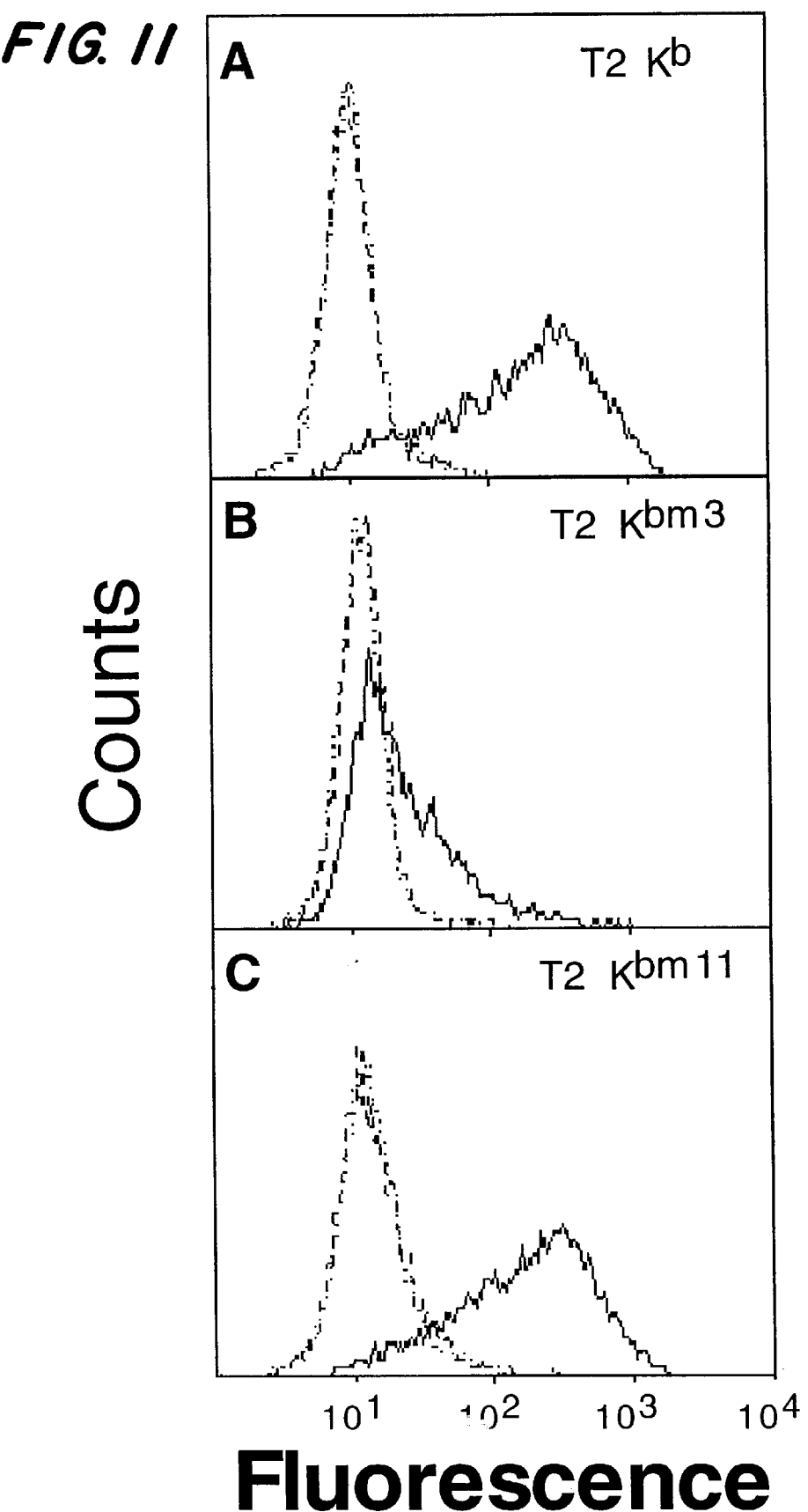
FIG. 11. Fluorescence data showing that soluble divalent 2C TcR/Ig interacts with SIY/MHC complexes but not with dEV-8/MHC complexes is depicted in FIG. 11. T2 cells transfected with either H-2 $K^b$, H-2 $K^{bm3}$, or H-2 $K^{bm11}$ were incubated overnight at 27° C. and loaded with peptides dEV-8 ( - - - ), SIY (QQ), or pVSV (aaaaa) as described below. Cells were stained with purified 2C TcR/Ig (~50 mg/ml) and GAM-IgG-RPE as described in Methods, and analyzed by FACS. Resultant histograms are shown; Panel A, T2-Kb cells; B, T2-$K^{bm3}$; C, T2-$K^{bm11}$. In the histograms presented 2C TcR/Ig reactivity with either dEV-8 ( - - - ) or pVSV (aaaaa) was virtually identical leading to difficulty in discriminating between these two histograms.
Figure 12:
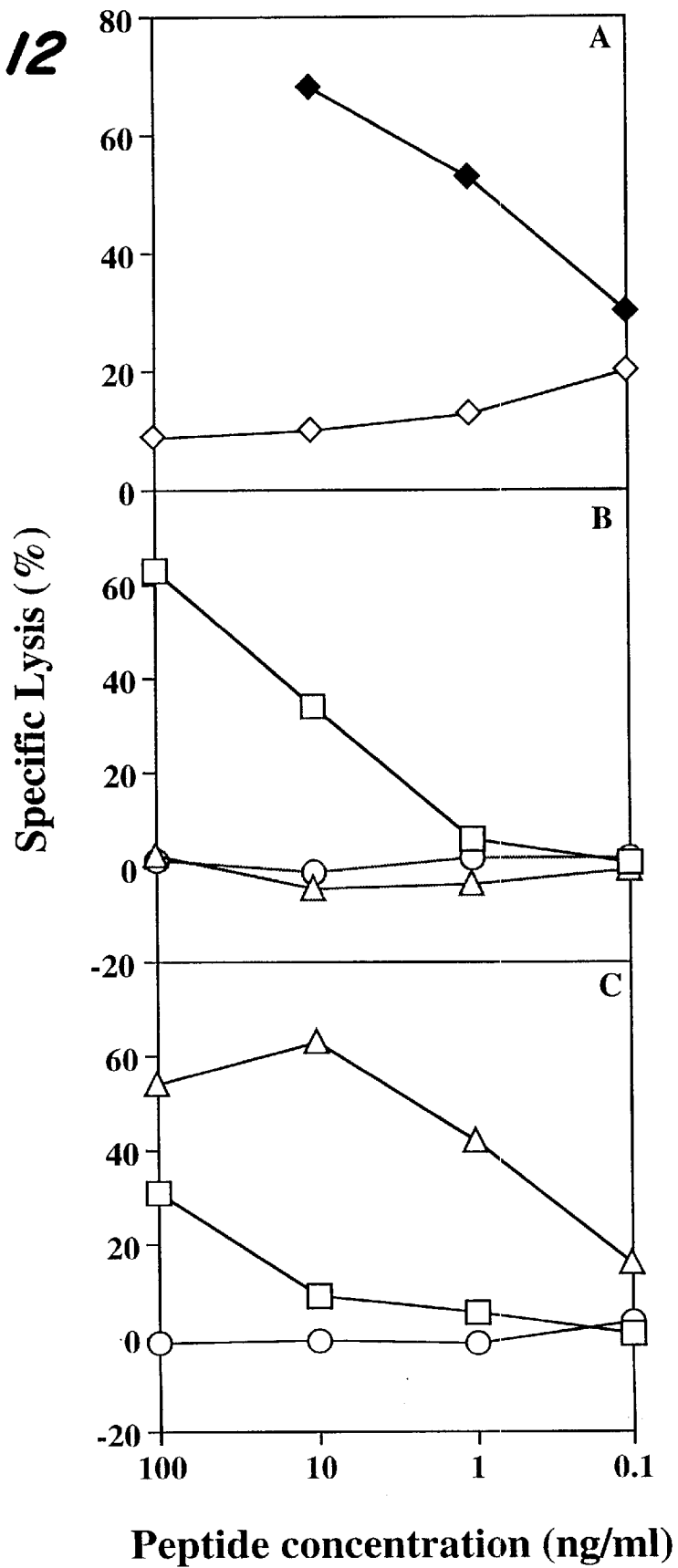
FIG. 12. 2C CTL mediated lysis on various peptide/MHC targets is depicted in this figure. T2 cells transfected with either H-2 $L^d$ (Panel A), H-2 $K^b$ (Panel B), or H-2 $K^{bm3}$ (Panel C), were chromium labeled as described and then loaded with peptides by incubating at 25{C for 1.5 hrs. in the presence of variable amounts of peptides: p2Ca ( ) and pMCMV ( ) (Panel A); and dEV-8 ( ); SIY ( ); or pVSV ( ) (Panels B and C). Peptide loaded target cells were then incubated at an effector to target ratio of 10:1 and specific lysis calculated as described below. Data shown are representative of three separate experiments.
Figure 13:
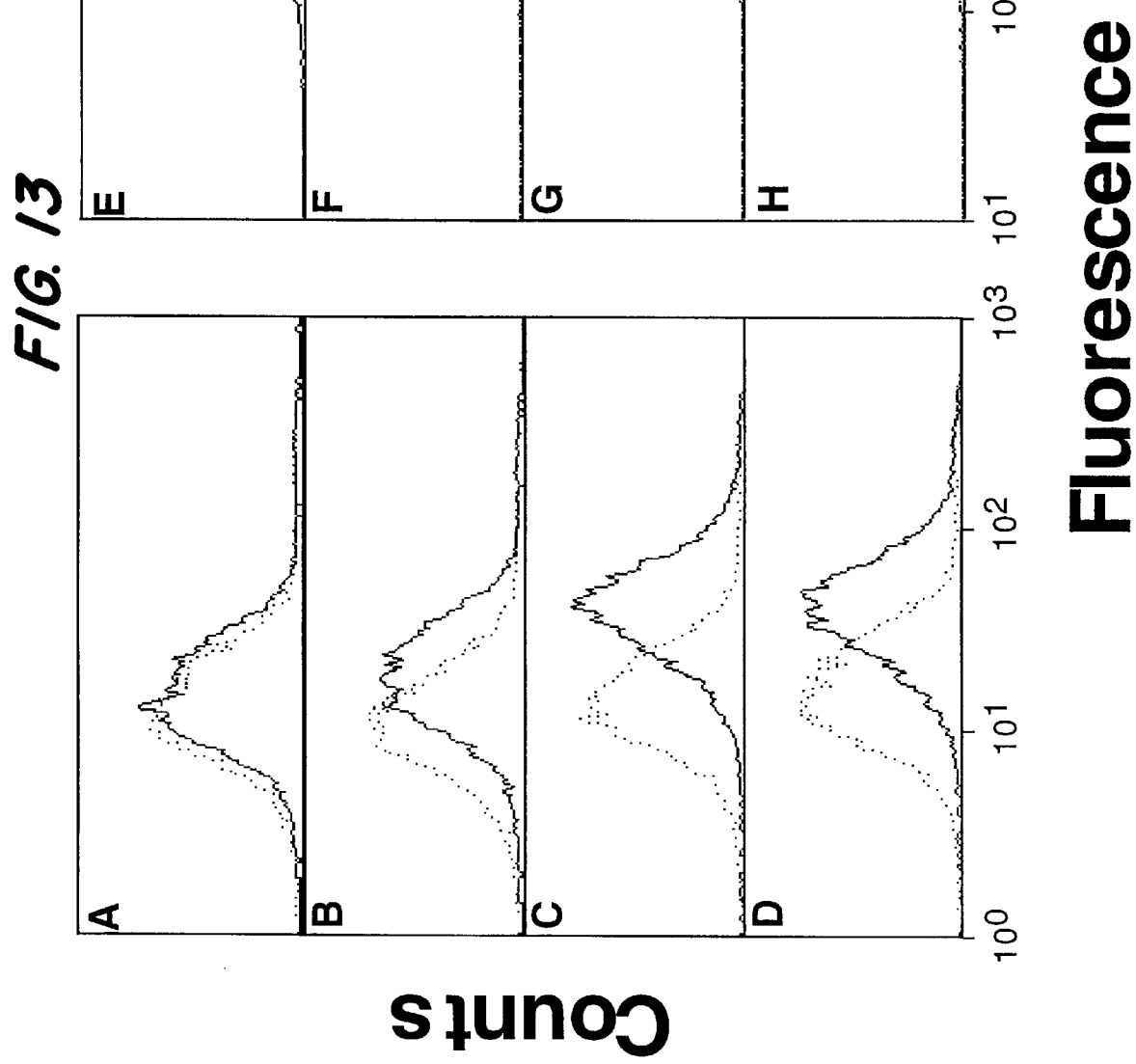
FIG. 13. Fluorescence data showing modulation of endogenous 2C specific peptide/H-2 $L^d$ complexes on the surface of RENCA cells by γ-IFN is depicted in FIG. 13. RENCA cells were cultured for 48 hrs. with 0 (panels A & E), 5 (panels B & F), 10 (panels C & G), or 50 (panels D & H), units/ml δ-IFN. As described in the results, δ-IFN is known to have a direct effect on class I expression, making it necessary to establish background binding of 2C TcR/Ig to δ-IFN treated cells. This was accomplished by incubating RENCA cells with saturating amounts of the H-2 $L^d$ binding peptide, MCMV, which efficiently displaced the endogenous H-2 $L^d$ bound peptides, including any 2C-reactive peptides. Cells were harvested, stained with 2C TcR/Ig (75 mg/ml), panels A–D, or the mAb 30.5.7 (45 mg/ml), panels E–H, as described below. Cells were subsequently stained with GAM-IgG-RPE and analyzed by FACS. Resultant histograms are shown. Solid lines (Q) represent histograms of cultures with no added peptide while dotted lines (aaa) represent histograms from cultures incubated with pMCMV. All experiments were done in duplicate and repeated at least three times. Note the differences in the extents of fluorescence (see the scales on the histograms) upon staining with 2C-TcR/Ig vs. staining with 30.5.7.

Peptide SIY-loaded T2 $K^b$ or T2 $K^{bm11}$ cells both expressed epitopes recognized by 2C TcR/Ig (FIG. 11A,C). MCF of cells incubated with 2C TcR/Ig increased approximately 20 fold from 14 for pVSV loaded—to 276 for SIY loaded—T2 $K^b$ and from 16 for pVSV loaded—to 250 for SIY loaded—T2 $K^{bm11}$. SIY-loaded T2 $K^{bm3}$ cells showed a much weaker but still significant interaction with 2C TcR/Ig (FIG. 11B); compare SIY-loaded (solid lines; MCF, 36) to pVSV-loaded (dotted lines; MCF, 12) T2 $K^{bm3}$ cells. The 2C TcR/Ig binding data to SIY/MHC complexes was consistent with 2C CTL mediated lysis on various SIY/MHC targets (FIG. 12). 2C CTL mediated efficient lysis of SIY loaded T2 $K^b$ and T2 $K^{bm11}$ cells (FIG. 12B and data not shown, LD50~10 ng/ml for SIY/T2 $K^b$). 2C CTL mediated lysis of SIY loaded T2 $K^{bm3}$ cells was significantly less efficient (FIG. 12C, LD50~100 ng/ml).

The binding of 2C TcR/Ig to dEV-8 loaded cells revealed a striking difference between the affinity of 2C TcR/Ig for dEV-8/MHC complexes and the ability of that same peptide/MHC complex to mediate lysis by 2C CTL. As expected, dEV-8 loaded T2 $K^b$ cells were neither lysed by 2C CTL (FIG. 12B), nor were they recognized by 2C TcR/Ig in flow cytometry assays (FIG. 12A). Interestingly, no significant binding of 2C TcR/Ig could be found to dEV-8 loaded T2 $K^{bm3}$ cells (FIG. 12B). MCF of cells stained with 2C TcR/Ig was similar whether cells were loaded with either dEV-8 or a control H-2 Kb-binding peptide, pVSV (FIG. 12; compare dotted to dashed lines). This is most surprising in that, consistent with previous reports (Tallquist et al (1996) supra, dEV-8 loaded T2 $K^{bm3}$ cells were efficiently lysed by 2C CTL (FIG. 12C). In fact, dEV-8 loaded T2 $K^{bm3}$ cells were much better target cells (LD50~0.5–1.0 ng/ml), than SIY loaded T2 $K^{bm3}$ cells (LD50~100 ng/ml), where a significant binding of 2C TcR/Ig was seen (FIG. 12B). The efficiency of lysis by 2C CTL of dEV-8 loaded T2 $K^{bm3}$ cells, was on the same order of magnitude as that of p2Ca loaded T2 $L^d$ cells (FIG. 12A, LD50~0.5 ng/ml) which was also efficiently recognized in the 2C TcR/Ig binding assay (FIG. 8). A similar, although significantly less dramatic, lack of correlation between cytolysis and 2C TcR/Ig binding was seen for dEV-8 loaded T2 $K^{bm11}$ cells. dEV-8 loaded T2 Kb $^{m11}$cells are relatively poor targets for 2C CTL (Tallquist et al (1996) supra) (data not shown), but were also not reactive with 2C TcR/Ig in flow cytometry assays (FIG. 11C).

Example 7

Analysis of the Effects of γ-IFN on Expression of Endogenous 2C-specific Peptide/MHC Complexes.

The specificity and affinity of 2C TcR/Ig for peptide/MHC complexes suggested that one might be able to use this reagent to probe the influence of lymphokines on endogenous, cell surface, peptide/MHC complexes. To analyze this possibility and follow the expression of endogenous 2C-reactive peptide/H-2 $L^d$ complexes within a heterogeneous peptide/MHC environment, the influence of γ-IFN on the H-2 $L^d$ expressing murine cell line, RENCA was studied. RENCA cells were cultured in the presence of variable amounts of γ-IFN to induce up-regulation of naturally loaded peptide/MHC complexes. 2C TcR/Ig binding to RENCA cells increased as a function of γ-IFN induction (FIG. 13A–D, solid lines). The effect of γ-IFN was dose dependent with a maximal 2–3 fold increase seen on cells treated with 10 units/ml of γ-IFN. Since γ-IFN is known to have a direct effect on class I expression (FIG. 13E–H) (Hengel et al Journal of Virology 68:289–297 (1994)), it is necessary to normalize for any non-specific 2C TcR/Ig binding secondary to increased expression of H-2 $L^d$. This was accomplished by incubating RENCA cells with a control irrelevant H-2 $L^d$ binding peptide, pMCMV. Since p2Ca is known to have a weak affinity for H-2 $L^d$ (Sykulev et al *Immunity* 1:15–22 (1994a) exchange with a higher affinity H-2 Ld binding peptide like pMCMV (Sykulev et al (1994a) supra) should be very efficient. Therefore background reactivity of 2C TcR/Ig could be determined by the efficient displacement of endogenous p2Ca or p2Ca-like peptides by incubating the cells with saturating amounts of the control pMCMV peptide. In all cases, 2C TcR/Ig binding could be blocked by prior incubation of cells with the control H-2 $L^d$ binding, pMCMV (FIG. 13A–D, dotted lines). Prior incubation of RENCA cells with a 2C specific peptide, QL9, induced a dramatic increase in 2C TcR/Ig binding (data not shown). The results of these experiments indicate that 2C TcR/Ig could be used as a sensitive probe to analyze cell surface expression of endogenous 2C-reactive peptide/MHC complexes.

The effect of γ-IFN on 2C TcR/Ig reactivity was distinct from its effects on 30.5.7 reactivity. At all concentrations analyzed, 5–50 units/ml, γ-IFN induced a 5–6 fold increase in serologically reactive H-2 $L^d$, as recognized by mAb 30.5.7 (FIG. 13E–H). MCF of unstimulated RENCA cells was 500, while the MCF of γ-IFN stimulated cells was between 2666 and 3038. The maximal effect of γ-IFN was seen at the lowest dose used, in the experiment presented, 5 U/ml, and in other experiments was seen even at dose of γ-IFN as low as 1 unit/ml (data not shown). Interestingly, the dose response curve of γ-IFN on 2C TcR/Ig reactivity was shifted. γ-IFN at 5 U/ml had a relatively small but significant effect on 2C TcR/Ig reactivity. Maximal effects of γ-IFN on 2C TcR/Ig reactivity required γ-IFN treatment at 10 units/ml, approximately ten fold more than needed for maximal effects of γ-IFN on 30.5.7 reactivity. These results indicate a differential effect of γ-IFN on MHC heavy chain expression than that of γ-IFN on specific peptide antigen/MHC complex expression.

These results show that this approach is a general one for producing soluble divalent versions of heterodimeric proteins. Soluble divalent analogs of heterodimeric proteins of this invention are characterized as having high avidity for their targets.

The same way that this was done for a single murine class II MHC and α/β TcR, so to the same technology, generating soluble divalent heterodimeric proteins, can be used to develop other mammalian systems. These will include both rodent and human class II HLA molecules and α/β and γ/δ T cell receptors.

The present invention may be embodied in forms other than those specifically disclosed above without departing from the spirit or essential characteristics of the invention. The particular embodiments of the invention described above, are therefore, to be considered as illustrative and not restrictive. All references and patent applications are herein incorporated by reference to the same extent as if each individual publication or patent application was specifically and individually indicated to be incorporated by reference.

REFERENCES

The following references are herein incorporated by reference:

Al-Ramadi, B. K., Jelonek, M. T., Boyd, L. F., Marguiles, D. H. and Bothwell, A. L. M. 1995. Lack of strict correlation of functional sensitization with the apparent affinity of MHC/peptide complexes for the TcR. J. Immunol. 155: 662–673.

Alam, S. M., Travers, P. J., Wung, J. L., Nasholds, W., Redpath, S., Jameson, S. C. and Gascoigne, N. R. J. 1996. T cell receptor affinity and thymocyte positive selection. Nature 38 1: 616–620.

Andersen, P. S., Stryhn, A., Hansen. B. E., Fugger, L., Engberg, J. and Buus, S. 1996. A recombinant antibody with the antigen-specific, major histocompatibility complex-restricted specificity of T cells. Proc. Natl. Acad. Sci. USA 193: 1820–1824.

Bikoff, E. K., Jaffe, L., Ribaudo, R. K., Otten, E. R., Germain, R. N. and Robertson, E. J. 1991. MHC class I surface expression in embryo-derived cell lines inducible with peptide or interferon. Nature 354: 235–238.

Boes, B., Hengel, H., Ruppert, T., Multhaup, G., Koszinowski, U. H. and Kloetzel, P. -M. 1994. Interferon γstimulation modulates the proteolytic activity and cleavage site preference of 20S mouse proteasomes. J. Exp. Med. 179: 901–909.

Catipovic, B., Dal Porto, J., Mage, M., Johansen, T. E. and Schneck, J. P. 1992. Major histocompatibility complex conformational epitopes are peptide specific. J. Exp. Med. 176: 1611–1618.

Connolly, J. M. 1994. The peptide p2Ca is immunodominant in allorecognition of $L^d$ by β chain variable region Vβ8$^+$ but not Vβ8$^-$ strains. Proc. Natl. Acad. Sci. USA 91: 11482–11486.

Corr, M., Slanetz, A. E., Boyd, L. F., Jelonek, M. T., Khiko, S., Al-Ramadi, B. K., Kim, Y. S., Maher, S. E., Bothwell, A. L. M. and Margulies, D. H. 1994. T cell receptor-MHC class I peptide interactions: affinity, kinetics and specificity. Science 265: 946–949.

Dick, T. P., Ruppert, T., Groettrup, M., Kloetzel, P. M., Kuehn, L., Koszinowski, U. H., Stevanovic, S., Schild, H. and Rammensee, H. -G. 1996. Coordinated dual cleavages induced by the proteasome regulator PA 28 lead to dominant MHC ligands. Cell 86: 253–262.

Duc, H. T., Rucay, P., Righenski, S., Halle-Pannenko, O. and Kourilshy, P. 1993. Monoclonal antibodies directed against T cell epitopes presented by class I MHC antigens. Int. Immunol. 5:427–431.

Fremont, D. H., Rees, W. A. and Kozono, H. 1996. Piophysical studies of T cell receptors and their ligands. Curr. Opin. Immunol. 8:93–100.

Froscher, B. G. and Klinman, N. R. 1986. Immunization with SV40-transformed cells yields mainly MHC-restricted monoclonal antibodies. J. Exp. Med. 164:196–210.

Garcia, K. C., Scott, C. A., Brunmark, A., Carbone, F. R., Peterson, P. A., Wilson, I. A. and Teytom, L. 1996. CD8 enhances formation of stable T cell receptor/MHC class I molecule complexes. Nature 384:577–581.

Groettrup, M., Ruppert, T., Kuehn, L., Seeger, M., Standera, S., Koszinowski, U. and Kloetzel, P. M. 1995. The interferon-γ-inducible 11 S regulator (PA28) and the LMP2/LMP7 subunits govern the peptide production by the 20 S Proteasome in vitro. J. Biol. Chem. 270:23808–23815.

Groettrup, M., Soza, A., Eggers, M., Kuehn, L., Dick, T. P., Schild, H., Rammensee, H. -G., Koszinowski, U. H. and Kloetzel, P. -M. 1996. A role for the proteasome regulator PA28α in antigen presentation. Nature 381: 166–168.

Hengel, H., Lucin, P., Jonjic, S., Ruppert, T. and Koszinowski, U. H. 1994. Restoration of cytomegalovirus antigen presentation by gamma interferon combats viral escape. Journal of Virol. 68:289–297.

Hogquist, K. A., Jameson, S. C., Heath, W. R., Howard, J. L., Bevan, M. J. and Carbone, F. R. 1994. T cell receptor antagonist peptides induce positive selection. Cell 76: 17–27.

Huang, A. Y. C., Gulden, P. H., Woods, A. S., Thomas, M. C., Tong, C. D., Wang, W., Engelhard, V. H., Pasternack, G., Cotter, R., Hunt, D., Pardoll, D. M. and Jaffe, E. M. 1996. The immunodominant major histocompatibility complex class I-restricted antigen of a murine colon tumor derives from an endogenous retroviral gene product. Proc. Natl. Acad. Sci. USA 93.

Jameson, S. C., Carbone, F. R. and Bevan, M. J. 1993. Clone-specific T cell receptor antagonists of major histocompatibility complex class I-restricted cytotoxic T cells. J. Exp. Med. 177:1541–1550.

Jameson, S. C., Hogquist, K. A. and Bevan, M. J. 1994. Specificty and flexibility in thymic selection. Nature 369:750–752.

Kranz, D. M., Sherman, D. H., Sitkovsky, M. V., Pasternack, M. S. and Eisen, H. N. 1984. Immunoprecipitation of cell surface structures of cloned cytotoxic T lymphocytes by clone-specific antisera. Proc. Natl. Acad. Sci. USA 81:573–577.

Leeuwen, A. V., Goulmy, E. and Rood, J. J. V. 1979. Major histocompatibility complex-restricted antibody reactivity mainly, but not exclusively, directed against cells from male donors. J. Exp. Med. 150:1075–1083.

Luescher, I. F. Vivier, E., Layer, A., Mahiou, J., Godeua, F., Malissen, B. and Romero, P. 1995. CD8 modulation of T cell antigen recpetor-ligand interactions on living cytotoxic T lymphocytes. Nature 373:353–356.

Matsui, K., Boniface, J. B., Steffner, P., Reay, P. A. and Davis, M. M. 1994. Kinetics of T cell receptor binding to peptide/I-$E^k$ complexes: Correlation of the diassociation rate with T cell responsiveness. Proc. Natl. Acad. Sci. USA 91: 12862–12866.

Murphy, D. B., Rath, S., Pizzo, E., Rudensky, A. Y., George, A, Larson, J. K. and Janeway, C. A., Jr. 1992. Monoclonal antibody detection of a major self peptide: MHC class II complex. J. Immunol. 148: 3483–3492.

Rabinowitz, J. D., Beeson, C., Wulfing, C., Tate, K., Allen, P. M., Davis, M. M. and McConnell, H. M. 1996. Altered T cell receptor ligands trigger a subset of early T cell signals. Immunity 5:125–135.

Schlueter, C. J., Schodin, B. A., Tetin, G. Y. and Kranz, D. M. 1996. Specificity and binding properties of a single chain T cell receptor. J. Mol. Biol. 256:859–869.

Schwartz, R. H. 1992. Costimualtion of T lymphocytes: The role of CD28, CTLA-4 and BB1 in interleukin-2 production and immunotherapy. Cell 71:1065–1065.

Seder, R. A., Paul, W. E., Davis, M. M. and De St. Groth, B. F. 1992. The presence of interleukin-4 during in vitro priming determines the lymphokine-producing potential of CD4+ T cells from T cell receptor transgenic mice. J. Exp. Med. 176:1091–1098.

Sha, W. C., Nelson, C. A., Newberry, R. D., Kranz, D. M., Russell, J. H. and Loh, D. Y. 1988. Positive and negative selection of an antigen receptor on T cells in transgenic mice. Nature 336:73–76.

Solheim, J. C., Alexander-Miller, M. A., Martinko, J. M. and Connolly, J. M. 1993. Biased T cell receptor usage by $L^d$-restricted, Tum peptide-specific cytotoxic T lymphocyte clones. J. Immunol. 150:800–811.

Solheim, J. C., Carreno, B. M., Myers, N. B., Lee, D. R. and Hansen, T. H. 1995. Peptide-induced rescue of serologic epitopes on class I MHC molecules. J. Immunol. 154:1188–1197.

Solheim, J. C., Carreno, B. M., Smith, J. D., Gorka, J., Myers, N. B., Wen, Z., Martinko, J. M., Lee, D. R. and Hansen, T. H. 1993. Binding of peptides lacking consensus anchor residue alters serological recognition of H-$2L^d$. J. Immunol. 151:5387–5397.

Spies, T., Cerundolo, V., Colonna, M., Cresswell, P., Townsend, A. and De Mars, R. 1992. Presentation of viral antigen by MHC class I molecules is dependent on a putative peptide transporter heterodimer. Nature 355:644–646.

Sykulev, Y., Brunmark, A., Jackson, M., Cohen, R. J., Peterson, P. A. and Eisen, H. N. 1994a. Kinetics amd affinity of reactions between an antigen-specific T cell receptor and peptide-MHC complexes. Immunity 1:15–22.

Sykulev, Y., Brunmark, A., Tsomides, T. J., Kageyama, S., Jackson, M., Peterson, P. A. and
Eisen, H. N. 1994b. High affinity reactions between antigen-specific T cell recptors and peptides associated with allogenic and syngeneic major histocompatibility complex class I proteins. Proc. Natl. Acad. Sci. USA 91:11487–11491.

Tallquist, M. D. and Pease, L. R. 1995. Alloreactive 2C T cells recognize a self peptide in the context of the mutant $K^{bm3}$ molecule. J. Immunol. 155:2419–2426.

Tallquist, M. D., Yun, T. J. and Pease, L. R. 1996. A single T cell receptor recognizes structurally distinct MHC/peptide complexes with high specificity. J. Exp. Med. 184:1017–1026.

Townsend, A. Ohlen, C., Bastin, J., Ljunggren, H. -G., Foster, L. and Karre, K. 1989a. Association of class I major histocompatibility heavy and light chains induced by viral peptides. Nature 340:443–448.

Townsend, A. Ohlen, C., , Foster, L, Bastin, J., Ljunggren, H. -G. and Karre, K. 1989b. Mutant cell in which association of class I heavy and light chains is induced by viral peptides. In Cold Spring Harbor Symposia on Quantitative Biology (Cold Spring Harbor, pp.299–308).

Udaka, K., Tsomides, T. J. and Eisen, H. N. 1992. A naturally occurring peptide recognized by alloreactive CD8+ cytotoxic T lymphocytes in Association with a class I MHC protein. Cell 69:989–998.

Udaka, K., Wiesmuller, K. -H., Kienle, S., Jung, G. and Walden, P. 1996. Self-MHC-restricted peptides recognized by an alloreactive T lymphocyte clone. J. Immunol. 157:670–678.

Van Bleek, G. M. and Nathanson, S. G. 1990. Isolation of an endogenously processed immunodominant viral peptide from the class I H-$2K^b$ molecule. Nature 348:213–216.

Wylie, D. E., Sherman, L. A. and Klinman, N. R. 1982. Participation of the major histocompatibility complex in antibody recognition of viral antigens expressed on infected cells. J. Exp. Med. 155:403–414.

We claim:

1. A first molecular complex which comprises at least four fusion proteins, wherein:
   (a) two first fusion proteins comprise (i) an immunoglobulin heavy chain, wherein the immunoglobulin heavy chain comprises a variable region, and (ii) an extracellular domain of a first transmembrane polypeptide; and
   (b) two second fusion proteins comprise (i) an immunoglobulin light chain and (ii) an extracellular domain of a second transmembrane polypeptide; wherein the fusion proteins associate to form the first molecular complex, wherein the first molecular complex comprises two ligand binding sites, each ligand binding site formed by the extracellular domains of the first and second transmembrane polypeptides, wherein the affinity of the first molecular complex for a cognate ligand is increased compared to a second molecular complex consisting of the extracellular domain of the first transmembrane polypeptide and the extracellular domain of the second transmembrane polypeptide.

2. The first molecular complex of claim 1 wherein the first transmembrane polypeptide is an MHC class IIβ chain and wherein the second transmembrane polypeptide is an MHC class IIα chain.

3. The first molecular complex of claim 1 wherein the first transmembrane polypeptide is a T cell receptor (TCR) α chain and wherein the second transmembrane polypeptide is a TCR β chain.

4. The first molecular complex of claim 1 wherein the immunoglobulin heavy chxxain is an IgG1 heavy chain.

5. The first molecular complex of claim 1 wherein the immunoglobulin light chain is an Igκ chain.

6. The first molecular complex of claim 1 wherein the first fusion proteins comprise a first peptide linker between the immunoglobulin heavy chain and the extracellular domain of the first transmembrane polypeptide and wherein the second fusion proteins comprise a second peptide linker between the immunoglobulin light chain and the extracellular domain of the second transmembrane polypeptide.

7. The molecular complex of claim 6 wherein the first peptide linker is GLY—GLY—GLY—THR—SER—GLY (SEQ ID NO: 10).

8. The molecular complex of claim 6 wherein the second peptide linker is GLY—SER—LEU—GLY—GLY—SER (SEQ ID NO: 11).

9. The first molecular complex of claim 1 wherein antigenic peptides are bound as ligands to the ligand binding sites.

10. The first molecular complex of claim 1 which is conjugated to a toxin.

* * * * *